(12) United States Patent
Alt et al.

(10) Patent No.: US 9,310,300 B2
(45) Date of Patent: Apr. 12, 2016

(54) COMPACT PORTABLE APPARATUS FOR OPTICAL ASSAY

(71) Applicants: Eckhard Alt, Houston, AZ (US); Jody Vykoukal, Houston, TX (US); Michael Coleman, Houston, TX (US)

(72) Inventors: Eckhard Alt, Houston, AZ (US); Jody Vykoukal, Houston, TX (US); Michael Coleman, Houston, TX (US)

(73) Assignee: INGENERON INCORPORATED, Houston, TX (US)

( * ) Notice: Subject to any disclaimer, the term of this patent is extended or adjusted under 35 U.S.C. 154(b) by 0 days.

(21) Appl. No.: 13/986,130

(22) Filed: Apr. 3, 2013

(65) Prior Publication Data

US 2014/0038222 A1    Feb. 6, 2014

Related U.S. Application Data

(60) Provisional application No. 61/679,300, filed on Aug. 3, 2012.

(51) Int. Cl.
    *G01N 21/01*    (2006.01)
    *G01N 21/63*    (2006.01)
    *G01N 21/64*    (2006.01)

(52) U.S. Cl.
    CPC .............. *G01N 21/63* (2013.01); *G01N 21/648* (2013.01); *G01N 21/6428* (2013.01); *Y10T 29/49002* (2015.01)

(58) Field of Classification Search
    CPC .................................................. G01N 21/63
    USPC .............................................. 435/288, 283.1
    See application file for complete search history.

(56) References Cited

U.S. PATENT DOCUMENTS

| 2009/0215072 A1* | 8/2009 | McDevitt et al. .............. 435/7.1 |
| 2011/0312724 A1* | 12/2011 | Facer et al. ...................... 506/39 |
| 2012/0157160 A1* | 6/2012 | Ozcan ................ G01N 21/6458 455/556.1 |

OTHER PUBLICATIONS

Hongying Zhu, Sam Mavandadi, Ahmet F. Coskun, Oguzhan Yaglidere, and Aydogan Ozcan, "Optofluidic Fluorescent Imaging Cytometry on a Cell Phone" Anal. Chem. 2011, 83, 6641-6647.*
Derek Tseng, Onur Mudanyali, Cetin Oztoprak, Serhan O. Isikman, Ikbal Sencan, Oguzhan Yagliderea, and Aydogan Ozcan, "Lensfree microscopy on a cellphone" Lab Chip, 2010, 10, 1787-1792.*
Motorola MotoZINE ZN5, Review Date Nov. 3, 2008, http://www.pcmag.com/article2/0%2c2817%2c2333745%2c00.asp?tab=Specs.*

* cited by examiner

*Primary Examiner* — Christopher A Hixson
*Assistant Examiner* — Emily Berkeley

(57) ABSTRACT

A structure is configured to retain optical diagnostic assay components in a manner that enables them to be synergistically combined or coupled both mechanically and electrically with a conventional mobile electronic device (such as a smartphone), such that the pairing maintains a mutually advantageous relationship to provide a compact portable optical assay apparatus in which the optical assay portion has access to the image sensor, battery power, microprocessor, and data capture, analysis, storage, display and transmission capabilities of the smartphone, and the smartphone portion provides the overall apparatus with features of transportability, user interface, and information storage, analysis and retrieval, and transmission of assay results to a separate site, such as a site of records related to the provider of the sample being assayed. Methods of providing such structure and of performing an optical assay of sample material utilizing such structure are described.

22 Claims, 10 Drawing Sheets

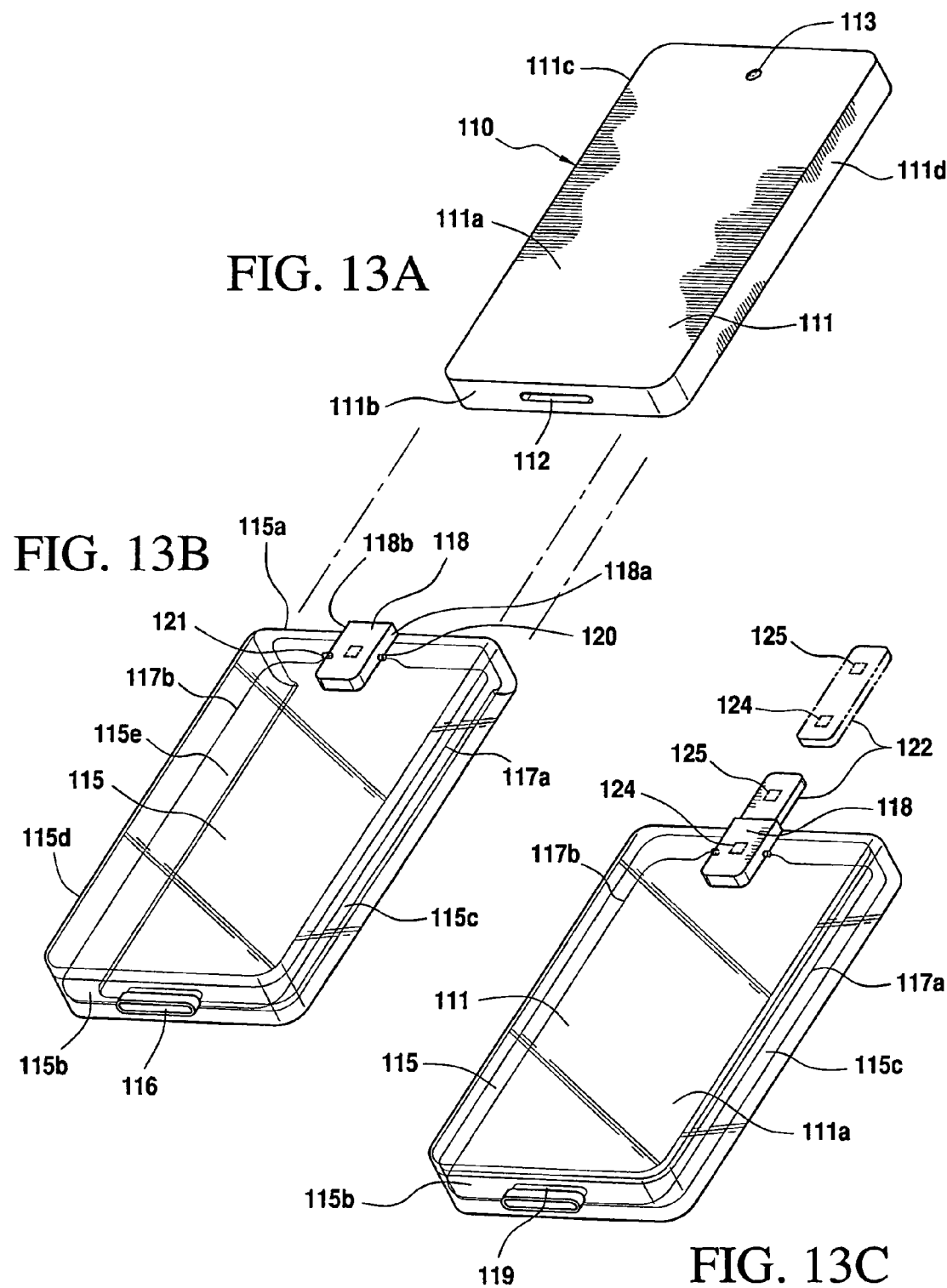

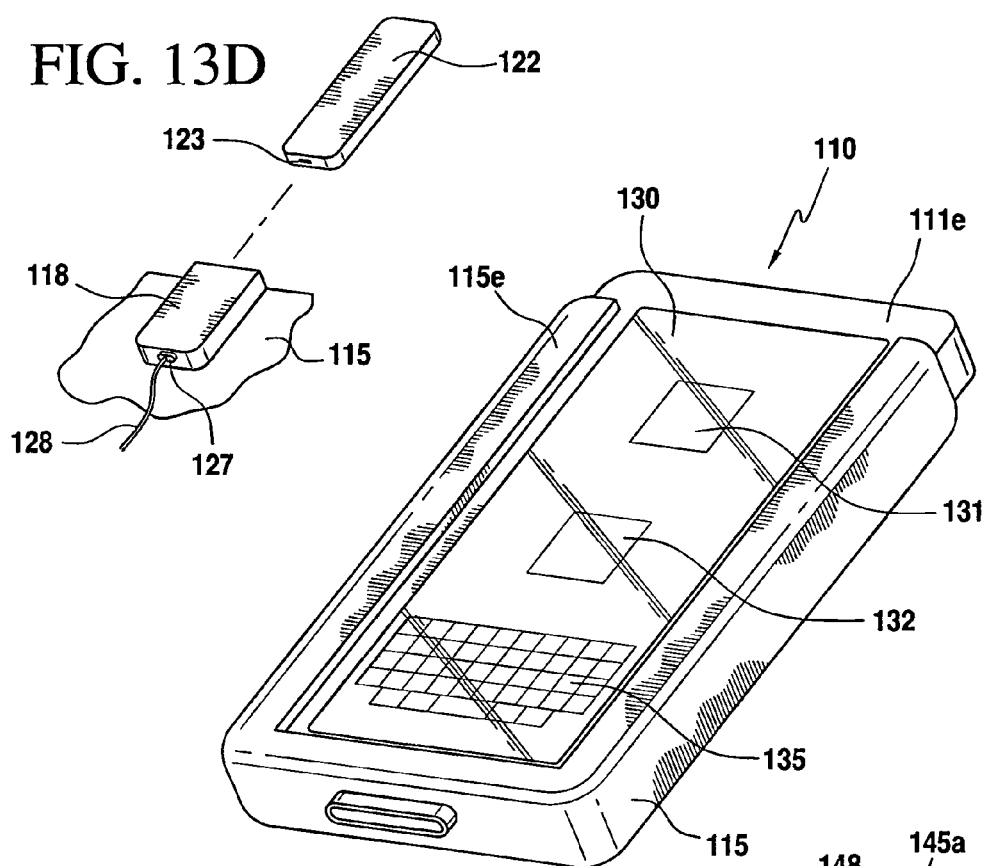
FIG. 13D
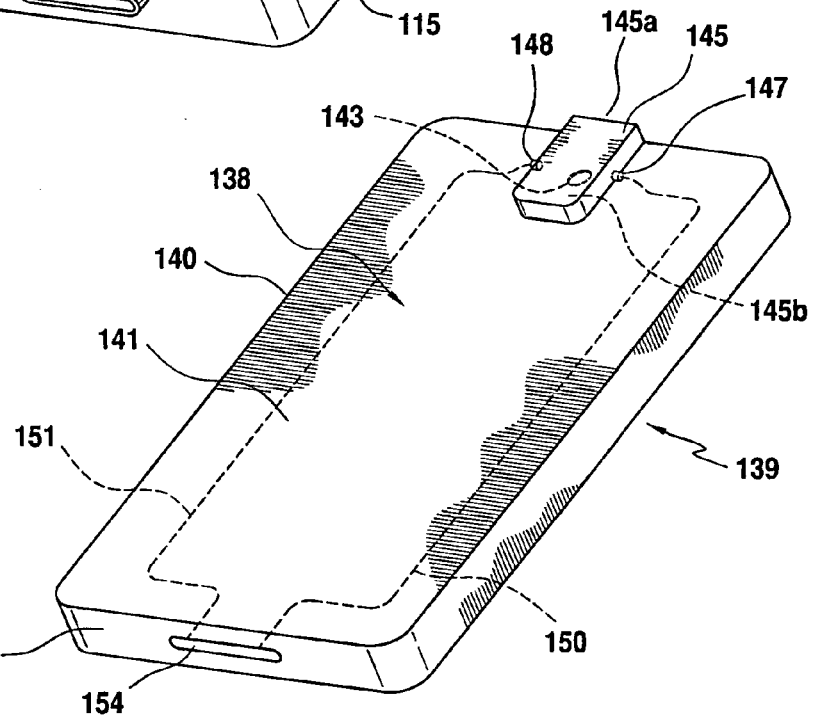
FIG. 14
FIG. 15

COMPACT PORTABLE APPARATUS FOR OPTICAL ASSAY

CROSS-REFERENCE TO RELATED APPLICATIONS

This application is related to U.S. Provisional Application No. 61/679,300, filed Aug. 3, 2012 by the same inventors herein ("the '300 provisional application"), as to which a claim of priority is made for common subject matter.

FIELD OF THE INVENTION

This invention relates generally to optical diagnostic assays of target analytes in sample specimens obtained from human or animal subjects, environmental sources, or foodstuffs, and more particularly to compact portable apparatus for performing the optical assays.

BACKGROUND OF THE INVENTION

Optical diagnostic assays are utilized to qualitatively and quantitatively detect chemical, biochemical, biological, cellular, and/or particulate species, sometimes referred to herein as analytes, in biological, clinical, environmental, or foodstuff samples. Performing such assays has been especially helpful, for example, in monitoring growing cell cultures and identifying and counting the number of particular cells of interest, such as cancer cells in a blood sample. In general, an assay consists of infusing selected fluorescent dyes, sometimes referred to herein as fluorophores, in a sample of a culture of interest to label and reveal cell types, from which to diagnose, investigate or monitor the progress of a specified disease and the extent to which a particular treatment regimen is successful (or ineffective) to arrest the disease in a human or animal subject.

The '300 provisional application addresses a need for simple, portable, inexpensive, and integrated assay and diagnostic approaches that are appropriate for use in minimal infrastructure, resource-limited settings such as those found in the developing world. Similarly, this need exists for use in resource-limited environments such as those encountered by emergency first responders, primary care physicians, patients at home, forensic investigators, and military field personnel. Optical detection approaches based on fluorescence, absorbance, or luminescence are frequently used methods in well-funded clinical and industrial laboratory analyses to quantify particulate, chemical or biochemical analytes including cells, subcellular components, and biomolecules. But such methods have not found widespread application in those resource-limited settings and environments primarily because of the complexity and cost of readout hardware for optical assays. In providing the improved assay and diagnostic approaches, the invention disclosed in the '300 provisional application offers advantages of considerably less complex and lower cost in medical and veterinary diagnostics, food safety and environmental testing, and other generalized analyte assessment at wide-ranging points-of-use, without suffering loss of accuracy.

Detection and readout of fluorescence-based assays utilizing typical stokes shift fluorescent reporter elements (fluorophores, or fluorescent chromophores) require detecting signals of relatively long wavelength (red-shifted) emission radiation from excited fluorophores. A problem in achieving the desired detection and readout arises from a need to do so amid a substantial background of comparatively shorter wavelength (blue-shifted) radiation used to excite the fluorphores. The excitation radiation is directed along or scattered towards the axis of detection of samples being assayed. And that radiation may be brighter than the fluorescence emitted from labeled analytes. To prevent the excitation radiation from overwhelming the emitted fluorescence and thereby to facilitate fluorescence detection, it is common practice to employ multiple light directing and filtering elements in the optical path between the assay sample and the detector. These elements are typically found in commercially available fluorescent microscopes, flow cytometers, microplate readers, and other fluorescent assay readout and detection systems.

With reference to FIG. 1, this array of prior art optical hardware 10 generally comprises the following basic optical components. A first bandpass filter (excitation filter) 11 allows passage of radiation wavelengths 15 from a broadband (white light) source 12, for exciting fluorophores in a sample 13 being assayed. A second bandpass filter (emission or barrier filter) 14 limits passage of radiation wavelengths 16 from the sample 13 corresponding to the fluorescent emissions 18 of the fluorphores employed to label the sample. A dichroic mirror 17 assists spatial separation of the excitation and emission radiation paths, the former path extending through an objective lens 19, and the latter path extending through an ocular lens 8 to a detector 9. These optical components are typically fabricated using one to five millimeter-thick glass substrates and contained within a filter cube, block, or wheel with characteristic dimensions of between two and ten centimeters. Typically, they are relatively fragile, bulky and expensive.

Fluorophores commonly used in readout and detection systems of the prior art optical hardware are excited primarily in the range between 359 nanometers (nm) (DAPI) and 649 nm (Cy5). The readout systems excite such fluorescent reporter elements (fluorophores) using broadband sources such as halogen lamps and short arc mercury or xenon gas discharge lamps, which are relatively inefficient from the standpoints of both bandwidth emission and power consumption. The wavelengths produced by these broadband sources range across a spectrum far wider than is needed to excite typical fluorophores. For example, a commonly used xenon arc lamp emits wavelengths greater than 700 nanometers, whereas nominal 30 nm-wide wavelength bands would serve for fluorescence excitation. By way of illustration, a portion of the graph of FIG. 7 (to be discussed in more detail presently) denotes the input power and total radiation of a mercury (hg) short arc source utilized for excitation of fluorescent reporter elements in some prior art systems. Although this source consumes 100 watts (W) of input power, it produces only about 0.1 W total radiation (i.e., 0.1% luminous efficiency, which constitutes the ratio of total luminous flux emitted to total input power) in the 460-500 nm blue band (a nominal 40 nm bandwidth) for FITC excitation. And filament, plasma, or gas broadband sources emit at typical overall luminous efficiencies in a somewhat better, but still power-wasteful range of from about 3.5% to about 8%.

Typical broadband sources employed in prior art readout and detection systems for optical assay of human and animal cells and other analytes are also characterized by relatively large size and considerable heat generation. These characteristics necessitate source placement in a housing sufficiently removed from the sample being analyzed to prevent deleterious effect on the resulting analysis. Similarly, the source must be suitably spaced from the collector, other lenses, fiber-optics, or other means utilized to transmit excitation radiation to the sample. The effect of this relatively wide spacing between elements is transmission loss and index mismatch that further exacerbate luminous efficiency of the overall system.

In general, medicine has traditionally employed application-specific hardware and software, often to perform computer-based analyses for diagnostic procedures. More recently, existing consumer platforms are being considered for medical applications. For example, consumer products such as mobile phones, smartphones, compact digital cameras, tablet computers and laptop computers (in particular, iPHONE® smartphones, WINDOWS® smartphones, ANDROID®-based smartphones and BLACKBERRY® smartphones, iPAD® and other tablet computers, PC (personal computer) and MAC® laptop computers—the marks designated by the superscript symbol ® are registered trademarks of their respective owners for the respective products generically listed immediately following the respective appearances of the marks) within the category of mobile electronic devices continue to progress in embedded computing power and memory. The increasingly rapid pace at which these improvements occur has been dramatic, and has not escaped the attention of practitioners concerning the potential use of such platforms in medical applications. Device designers and manufacturers have exponentially increased the digital imaging systems within internet accessible mobile phones and other consumer electronic devices. Currently, image sensors (also known as photosensor arrays, or camera chips) with resolution of more than 20-megapixels are available to consumers on a widespread basis.

It is a principal aim of the present invention to provide a compact, portable, handheld optical assay system by combining or coupling an optical assay apparatus with a mobile electronic device in a synergistic manner to provide improved capabilities for performing optical assays. Mobile electronic devices are often capable of wirelessly accessing the internet or other communication networks, as well as the cloud. Thus, an optical assay system resulting from the coupling of an optical assay apparatus to such a wireless mobile electronic device would enable assay systems capable of performing assays at discrete points of need, and yet also able to exchange information via global communication infrastructure.

Moreover, it is a primary goal of the invention to enable the coupled optical assay apparatus to exploit the applications (colloquially referred to as "apps"), functions including image sensing, and battery power of the mobile electronic device, and to enable the coupled device to exploit the results of the assay performed by the optical assay apparatus for analysis, processing, comparison with a standard, viewing, storage and selective transmission thereof to a separate site, whether local or remote.

Another important objective is to enable performance of optical assays with apparatus attachably and removably coupled to widely available conventional mobile electronic devices, for synergy therebetween as well as compactness and portability of the enhanced apparatus, with an additional advantage of suitability for low-cost transport to and use in environments where apparatuses for performing optical diagnostic assays are otherwise unavailable.

Yet another aim of the invention is to provide methods of performing such assays, and methods of coupling the assay components and the mobile electronic device together to attain such capabilities.

BRIEF SUMMARY OF THE INVENTION

To attain these and other aims, goals and objectives, the optical assay excitation and reader hardware is connected to or integrated with the optical components and path of digital imaging systems of a mobile electronic device such as a mobile phone, smartphone, digital camera, tablet or laptop computer, for example, and more generally sometimes referred to herein in assembled (i.e., coupled or combined) form as adapted mobile electronic devices or compact portable optical assay apparatus. Preferably, the device is capable of wireless transmission and reception. Among other things, this assembly takes advantage of the intrinsic (i.e., built-in) capability of the mobile electronic device to adjust and control image sensor functions including light exposure, resolution and focusing, and to provide battery power. In addition, the invention utilizes the computing and wireless transmission capabilities of the adapted mobile electronic device and the digital imaging system to analyze, process, archive, or transmit optical information or images regarding the acquired optical assay data for various applications, preferably medical.

A further objective of the present invention is to advantageously utilize widely available image processing and analysis software, such as NIH (National Institutes of Health)-designated IMAGE™ (trademark of its owner for image processing/analysis software), or other public/private domain image processing software or libraries, which can be downloaded and stored in the adapted mobile electronic device memory. This software may then be used, alone or in conjunction with customized application specific software programs, to process and analyze digital data including but not limited to optical information or images obtained during optical assays with the adapted mobile electronic device.

The present invention also aims to provide means employing the capabilities of the adapted mobile electronic device to store the acquired and computed or analyzed optical data, for assignment to a specific memory or file, such as a particular patient's file or record accessible by the patient's attending physician. Additionally, it is an object of the invention to use the internet-accessible capability of the adapted mobile electronic device to transfer the raw and/or computed data from the device memory to another device or to a facility such as a hospital or clinic. Data may be transmitted in encoded form to protect patient privacy if required, or non-encrypted if a requirement of privacy is not mandated. Such data may be transmitted to a recipient having a capability to link it with an electronic patient record by a defined healthcare informatics interoperability standard (HL7 Clinical Document Architecture, i.e., Health Level 7, published as standard ISO/HL7 21731:2006, for example) to enable its entry into the electronic file of a specific patient.

The adjunct coupling structure, or coupler, utilized to combine the two portions may include a light source(s) for the optical assay, powered by the battery of the mobile electronic device portion of the assembly. To that end, an appropriately outfitted electrical plug or male connector such as a USB or APPLE® (registered trademark of its owner for multiplicity of products) LIGHTNING™ (trademark of its owner for the following product) connector, compatible with the mobile electronic device, may be integrated into the coupler and electrically connected to the light source(s) via a lead or cable within the coupler wall. Such an arrangement allows mating of the coupler's male connector with the female connector of the mobile electronic device for access to the battery power thereof. Advantageously beyond such usage, the mating of the coupler connector and the device connector serves to improve mechanical stabilization between the assay portion and the device portion when the two are joined, as well as to enable exchange of information between the two portions.

In a presently preferred embodiment, the coupler structure has the form of a frame, an outer casing, housing or holder (hereinafter generally referred to as a coupler) implemented to be slid, preferably snugly, over the case (or to snugly receive the case) of the mobile electronic device and, incidental thereto, to allow the mating electrical connectors of the two to engage for enabling access to battery power of the mobile electronic device by the optical assay portion when an assay is performed. Light source(s), lenses and other optical components, as well as light guides (i.e., optical waveguides) and retainer(s) of the sample specimen(s) to be used in the optical assay(s) may be integrated with or supported by the coupler itself. An alternative arrangement provides the light source(s) and associated optics within or on a cartridge with a reservoir for the sample.

In essence, the present invention in one of its principal aspects may be defined broadly as a compact portable optical assay system comprising an optical assay portion mechanically coupled to a mobile electronic device with optical information acquisition capability, wherein the coupling enables optical communication between the assay portion and the device for acquisition by the device of optical information related to a sample to be assayed confined in the assay portion. The optical information to be acquired by the device relates to identifying at least one type of analyte among cellular, chemical, biological, and particulate analytes potentially present in the sample being assayed.

The device is preferably battery-powered, and the coupling enables the assay portion to be powered by the device battery. An alternative source of power may be used, such as from the device charger (which may be a solar-energized charger, in contrast to an standard charger), for example, thereby accomplishing both charging of the device when depleted, and powering the assay portion. The coupling further enables electrical communication between the assay portion and the device. Preferably, the device includes an image sensor for capturing optical signals (i.e., optical information) that emanates from the sample analytes when properly illuminated by a light source, a display to enable viewing of the optical information acquired during the assay, memory to enable storage of that information for subsequent viewing and analysis, and transmission capability to enable transmission of the information from the device to a separate location, which may be local relative to or remote from the site at which the assay is performed. The device also includes software (and typically microprocessor function) for processing the information by the device, to be available for the aforementioned acquisition, viewing, storage, analysis and transmission.

As noted above, a preferred mobile electronic device for use in embodiments and methods of the invention includes one of a smartphone, a tablet computer, and a laptop computer, each of which possesses the aforementioned functions and capabilities.

Alternatively, the invention may be defined in another of its aspects as compact apparatus for facilitating the performance of optical assays, comprising a mechanical coupler including a receptacle for a sample containing analytes to be assayed, a light source for illuminating the sample with light conducive to the assay, and an enclosure adapted to receive and retain an electronic device having an electrical power source, image sensor, microprocessor, and data storage media; wherein the coupler is arranged and adapted (i) to allow optical communication between the sample and the device such that when the sample is illuminated by the light, optical information concerning analytes therein is routed to the image sensor, and (ii) to transfer power from the power source to the light source for illumination of the sample, whereby to enable detection of optical information related to the assay being performed.

The light from the source(s) utilized to illuminate the sample occupies a preselected wavelength band, which may be selected by the user from among plural wavelength bands, according to the analyte (and reporter element interacted therewith) sought to be detected and identified in the assay. The receptacle for the sample may be adapted to receive and retain a cartridge containing the sample on which the assay is to be performed, and the light source(s) may be strategically mounted on the coupler or, alternatively, in the cartridge itself, to illuminate the sample upon a transfer of power to the light source(s) by the coupler. Miniaturized optical devices such as waveguides, lenses, filters, etc. may be utilized on the coupler or in the cartridge to direct and intensify the light illuminating the sample.

The mobile electronic device should possess wireless transmission and reception capability to enable, among other purposes mentioned herein, downloading of data and programs from the Internet or cloud onto the storage media of the device, for usage in acquisition and processing of the optical information, as well as for comparison with data designated as a standard by an official agency or department.

As another alternative, the present invention may be defined as a combination of a mobile electronic device and an optical assay apparatus, the assay apparatus including a reservoir adapted to receive samples to be assayed, wherein designated target analytes in the sample are to be detected from optical signals emitted by the target analytes; the assay apparatus being secured to but readily separable from the device; a light source operatively associated with the reservoir and arranged to expose the target analytes in the sample to light emanating from the source to cause said optical signals to be emitted; the device including an image sensor for detecting the optical signals emitted by the target analytes.

In this embodiment, the reservoir may be contained in a cartridge adapted to be inserted into the assay apparatus, rather than provided in some other fashion. In any case, the elements are arranged to position the sample in optical communication with the light emanating from the source and with the image sensor.

In another aspect of the invention, optical assay apparatus is provided for operation in conjunction with a mobile electronic device capable of storage and transmission of data obtained from optical information detected by an integral image sensor; the assay apparatus including a holder for a sample to be assayed, a light source for directing light onto a sample contained in the holder, and an optical path for directing optical information from the sample to the image sensor, so as to detect characteristics of the sample ascertained from the optical information.

The invention may be defined in another of its aspects as a structure to facilitate optical assay of samples potentially of at least one of cellular, chemical, biological, and particulate analyte content, comprising a sample reservoir, a light source for illuminating a sample in the reservoir with light conducive to the assay, an optical waveguide configured for optically coupling the reservoir to the light source, the light source having a viewing angle sufficiently narrow to promote total internal reflection within the waveguide of light emitted by the source, for maximum incidence thereof on the sample.

The invention may be defined alternatively as a method of providing a compact portable handheld optical assay system, comprising synergistically coupling an optical assay apparatus with a mobile electronic device, to enable detection of optical signals emanating from a target analyte in a sample under assay with an image sensor of the device.

Yet another aspect of the invention may be defined as a method for performing an optical diagnostic assay of a sample with a mobile electronic device, including the steps of exposing the sample to a reporter element designed to interact with analytes of interest potentially present in the sample and adapted to emit an optical signal, loading the sample into a reservoir supported on the mobile electronic device, capturing optical signals emanating from the sample with an integral image sensor of the mobile electronic device optically coupled to the reservoir to detect analytes of interest therein for assaying the sample; and processing, analyzing and storing data representative of the captured optical signals in data memory of the mobile electronic device, utilizing software application programs of the device.

Still another aspect of the invention may be recited as a method of performing an optical assay of a sample with a wireless mobile electronic device adapted to be handheld and having image sensing, computing, control, data storage, and electrical signal transmission functions, including the steps of labeling analytes of interest within the sample with a reporter element adapted to emit an optical signal in response to irradiation of the sample with light in a predetermined bandwidth, coupling a reservoir containing the labeled sample with the device, irradiating the labeled sample with light in the predetermined bandwidth, detecting optical signals emanating from analytes of interest with the image sensing function of the device; and processing, analyzing and storing data representative of the detected optical signals utilizing software applications of the device.

BRIEF DESCRIPTION OF THE DRAWINGS

The above and other aims, objectives, aspects, features and advantages of the invention will be better understood from a consideration of the following detailed description of the best mode contemplated for practicing the invention, taken with reference to certain preferred implementations and methods, and the accompanying drawings in which:

FIGS. 13A, 13B and 13C represent an exploded perspective view of an exemplary mobile electronic device, here a conventional smartphone, viewed at its back (13A), and a coupler (13B) implemented for synergistically combining the device with an optical assay cartridge in an assembled form (13C), according to a preferred embodiment of the invention; and FIG. 13D is a simplified enlarged exploded and fragmented perspective view of an alternative scheme for electrically connecting an optical assay cartridge to the device battery via the coupler;

FIG. 14 is a simplified perspective view of the front of the smartphone of FIG. 13A, illustrating the display screen of the phone and control thereof;

FIG. 15 is a simplified perspective view of the back of a smartphone modified to accept another type of coupler, according to an alternative embodiment;

The Figures are not intended to be to scale, nor to do more than serve as a visual aid to the description. Certain components may be exaggerated relative to others for the sake of emphasis or clarity of the respective accompanying description.

DETAILED DESCRIPTION OF THE INVENTION

To overcome the luminous inefficiencies of optical assay apparatus of the prior art, and assist in achieving improved, low-cost, and portable fluorescence readout and detection apparatus, the present invention employs relatively tiny light sources such as light emitting diodes (LEDs). Used in a prototype implementation of the invention, LEDs have demonstrated overall luminous efficiencies approaching 40-45% (see FIG. 7, for example). Unlike typical sources of broadband radiation, LEDs emit photons via the mechanism of electroluminescence, with radiation wavelengths that may be tuned to a relatively narrow range according to the band gap energy of the semiconductor or other organic material used to fabricate the source. This enables matching emission wavelengths with peak absorption wavelengths of various fluorescent reporter elements to eliminate the need for bandpass excitation filters. Indeed, as much as 100% of the wavelength band emitted by a suitably selected LED can be applied for excitation of a particular fluorophore.

Figure 1:
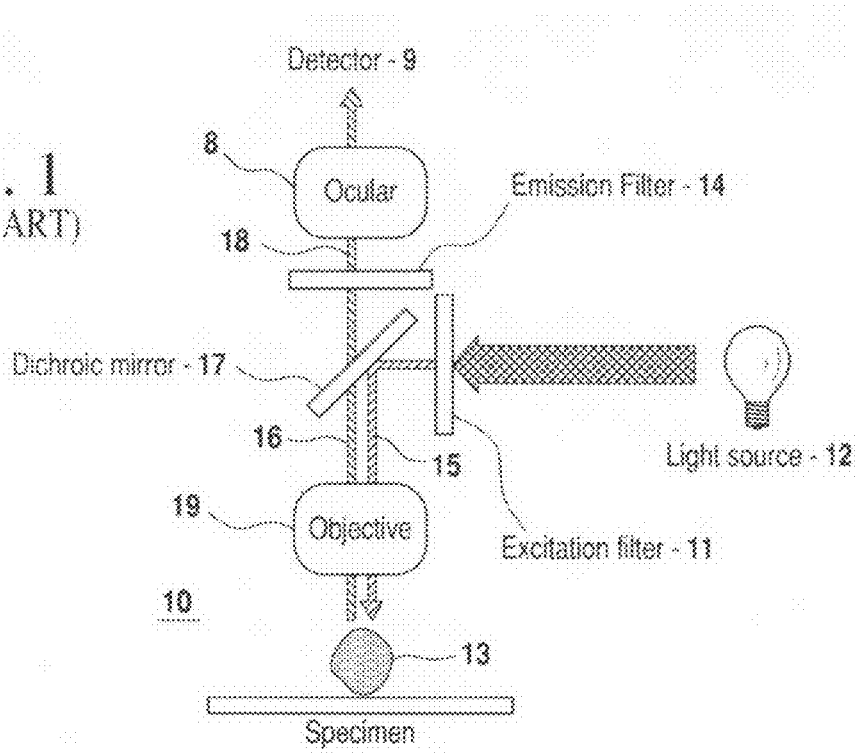
FIG. 1 illustrates the set-up of a typical optical assay system of the prior art, described above.
Figure 2A:
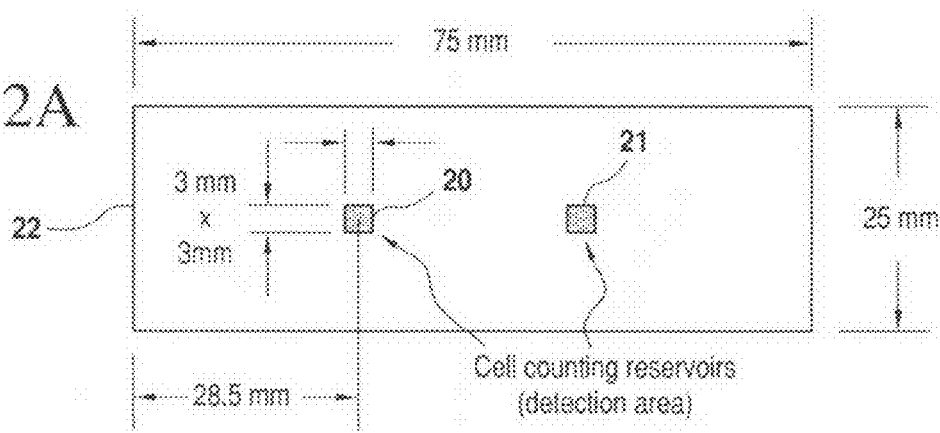
FIGS. 2A and 2B are simplified top and bottom views, respectively, of a portion of an exemplary optical assay apparatus of the invention containing standard manual Neubauer hemocytometers.
Figure 2B:
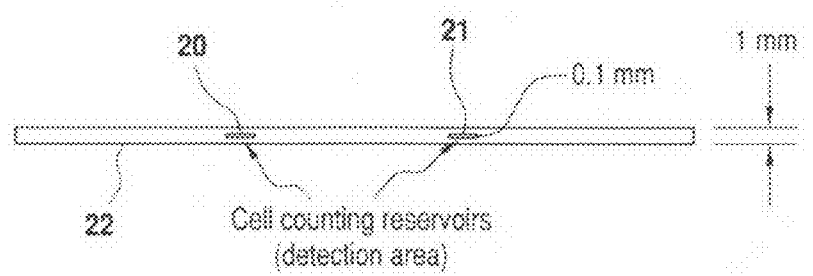

The invention may be characterized in part by a microminiaturized embodiment in which a solid-state excitation source is optically coupled via an index-matched adhesive or low-loss mechanical means to a reservoir for a sample that contains labeled target analytes, so as to maximize transfer of excitation radiation from the source to the sample. An exemplary arrangement is illustrated in simplified form in the top and side views of FIGS. 2A and 2B, respectively. According to an aspect of the invention, manual cell counting assays are typically performed using a standard manual Neubauer hemocytometer, that is, a fixed volume chamber (e.g., 20) measuring 3 mm×3 mm×0.1 mm that contains 900 mL of cell suspension. Cells to be assayed are incubated with a cell viability labeling reagent, such as viability nucleic acid, and loaded into the hemocytometer. In the Figures, two hemocytometers 20, 21 are shown within a single low-loss microsized optical substrate 22 to allow assaying two different samples.

The labeling reagent(s) may be preloaded into the sample reservoir configured to allow cells to be loaded directly into the analysis chamber without the requirement of a separate labeling step. Sample preparation cartridges may also contain filters, microfluidic features, volume calibrated reservoirs, reagents, or other elements to enable load-and-go sample preparation for optical analyses. To accomplish these and other ends, the optical assay hardware preferably utilizes microscale components and phenomena to enable compact, relatively simplified and easily fabricated arrangements for performing optical assays. These arrangements enable enhanced guiding of optical radiation for excitation and detection of reporter labeled assay samples, and provide highly efficient means to differentiate fluorescence or other optical signals from excitation radiation or off-target scatter. These solutions involve the use of materials, thin film fabrication, and methods that exploit refractive index differences to direct and filtered light.

Figure 3A:
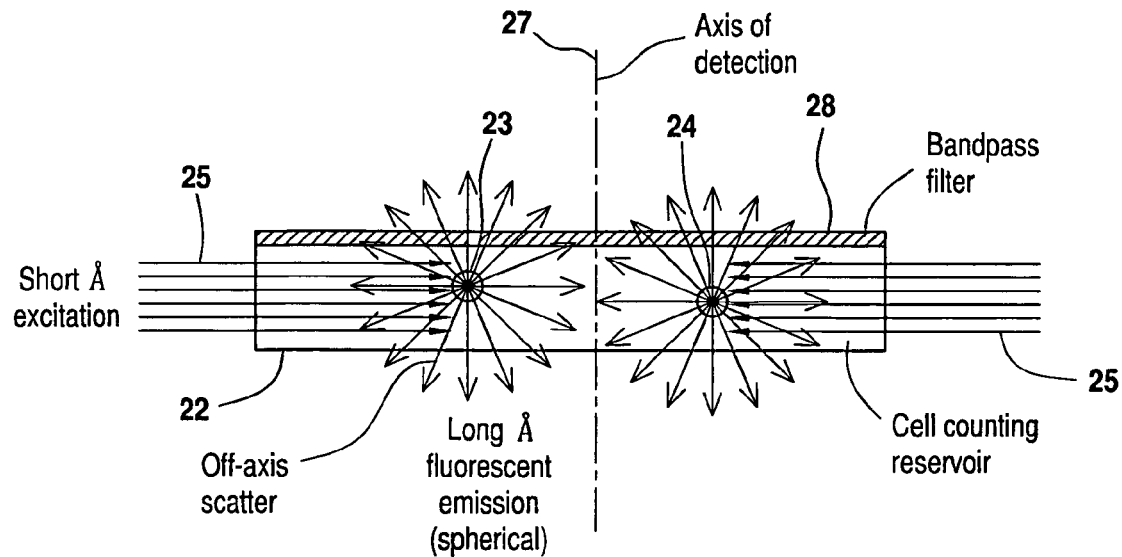
FIGS. 3A and 3B are simplified side and top views, respectively, of a portion of an exemplary miniaturized optical assay apparatus (i.e., compact, in keeping with the size of a conventional smartphone, for example, to which it is to be coupled) embodying a portion of the invention, illustrating the direction of excitation radiation and of fluorescent emission including scatter from a target analyte, and the detection axis.

It is noteworthy that miniaturization of the optical assay apparatus is a significant consideration toward achieving a component of the overall system that presents a suitable approximate match with the size of the mobile electronic device with which that component is to be coupled. An exemplary miniaturized implementation and approach is illustrated in FIG. 3A, an enlarged side view of a portion of the optical assay apparatus viewed from the short dimension end of the top view of FIG. 3B. Short Å excitation radiation 25 is directed from either side of the reservoir (e.g., 20 and/or 21) along an axis normal to the preferred axis of detection 27 to eliminate the requirement for a dichroic mirror or other means to spatially separate the excitation and emission radiation paths. The excitation radiation is directed through a nominal one millimeter thick glass, plastic, or other optically transparent substrate 22 that includes a reservoir (e.g., 20) containing the sample being assayed. The substrate and sample suspending medium both function as planar waveguides to direct light from the excitation source to reporter elements such as fluorophores or nanoparticle scatter labels (e.g., 23, 24) within the sample. Fluorescent emission or scattered radiation originating from reporters 23, 24 on a target analyte radiate from the reporter element spherically or at an angle (indicated as off-axis scatter) from the axis of excitation 25 and may, therefore, be detected along an axis different from the axis of excitation. In the preferred implementation, the axis of detection 27 for the long Å fluorescent emission is perpendicular to the axis of excitation, rather than along other off-axis scatter. A thin film bandpass filter 28 is deposited along a surface of the substrate/reservoir nearest the detector.

Figure 3B:
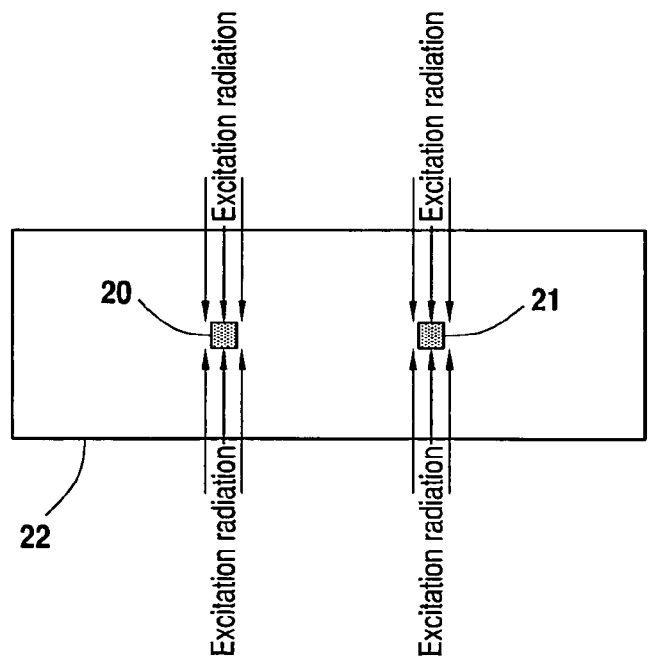
Figure 4:
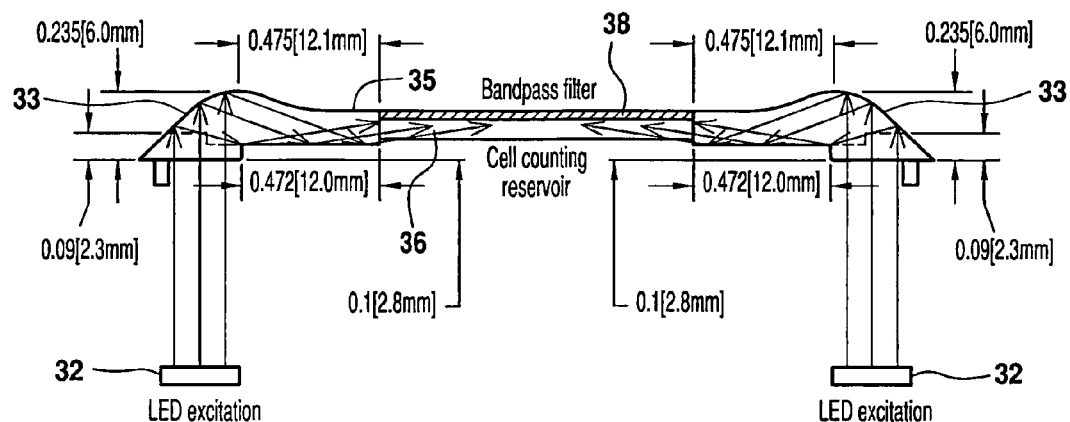
FIG. 4 is an end view of a portion of an alternative miniaturized configuration or implementation of an optical assay apparatus.

FIG. 4 is an end view of a portion of an alternative configuration or implementation of a miniaturized optical assay apparatus, illustrating exemplary dimensions. Instead of directing excitation radiation into the sample reservoir from a source oriented to produce radiation directly along the axis of excitation as shown in FIGS. 3A, 3B, the light source(s) (preferably, LED) 32 may be arranged relative to the light path of the reservoir with which each source is operatively associated, to produce excitation radiation along a different axis, normal to its initial direction. This allows the precise configuration of the compact optical assay apparatus of the invention to be selected for the most appropriate arrangement of its elements in the final array. To that end, the excitation radiation from light source 32 is deflected by a mirror or lens 33 appropriately angled to direct the reflected light along an auxiliary waveguide (i.e., an optical waveguide) 35. The excitation radiation is thus diverted along a primary axis of excitation to impinge on the reservoir 36 and the sample specimen (e.g., blood cells or human tissue cells) contained therein, in which the targeted particulate matter to which fluorophores are bound are suspended. Light emitted from the bound reporters on the particles is subjected to bandpass filtering by an appropriate film 38 applied to the surface of reservoir adjacent to the location of the detector.

Figure 5:
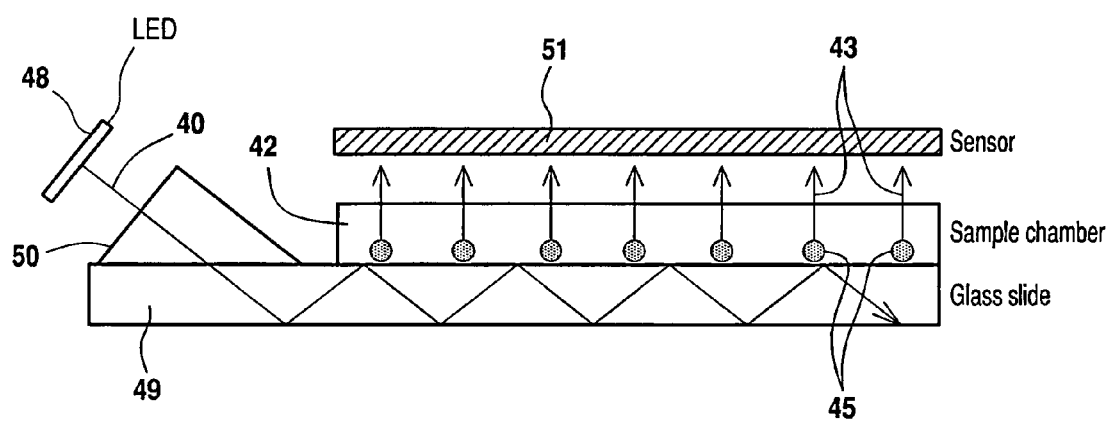
FIG. 5 is a simplified diagram of another alternative miniaturized embodiment of a portion of an optical assay apparatus.

FIG. 5 is a simplified diagram of another alternative embodiment of a portion of the optical assay apparatus, illustrating a further approach for its miniaturization. Excitation radiation 40 in the form of light in a preselected wavelength band from an LED 48 is directed onto a sample 42 to be assayed. Resulting radiation 43 emanating from fluorescing reporter elements 45 bound to analytes in the sample chamber is detected by a sensor 51. Here, the excitation radiation 40 is generated by selective activation of an LED source 48 operatively associated with the sample chamber at a predetermined angle thereto. The excitation radiation enters a glass substrate 49 via a prism 50 having a refractive index matching that of the substrate. The angle of incidence of the excitation at entry is greater than the critical angle defined by the respective refractive indices of the substrate 49 and its surrounding media (in this example, air or aqueous buffer). Because the refractive index of the surrounding media is lower than that of the substrate, rays of excitation light are reflected at the medium boundary (i.e., the boundary between the substrate and the sample chamber on one side and the medium surrounding the glass substrate on its other sides). This phenomenon of total internal reflection is promoted by the arrangement to effectively confine the majority of the excitation radiation 40 within the substrate 49.

However, a finite portion of this light propagates beyond the substrate 49 boundary into the reservoir chamber 42 as an evanescent wave, which is sufficient to excite reporter elements bound to analytes 45 suspended in the labeled sample in close proximity to the surface of the substrate 49 in contact with the chamber. A portion of the resulting emitted radiation 43 from the reporter elements is incident on and detected by an image sensor 51. Because the intensity of the evanescent wave propagated beyond the substrate decays exponentially, it is present in the vicinity of this emitted radiation as background radiation only, and is inadequate to substantially affect or alter the detection of the emitted radiation by the sensor.

Figure 6:
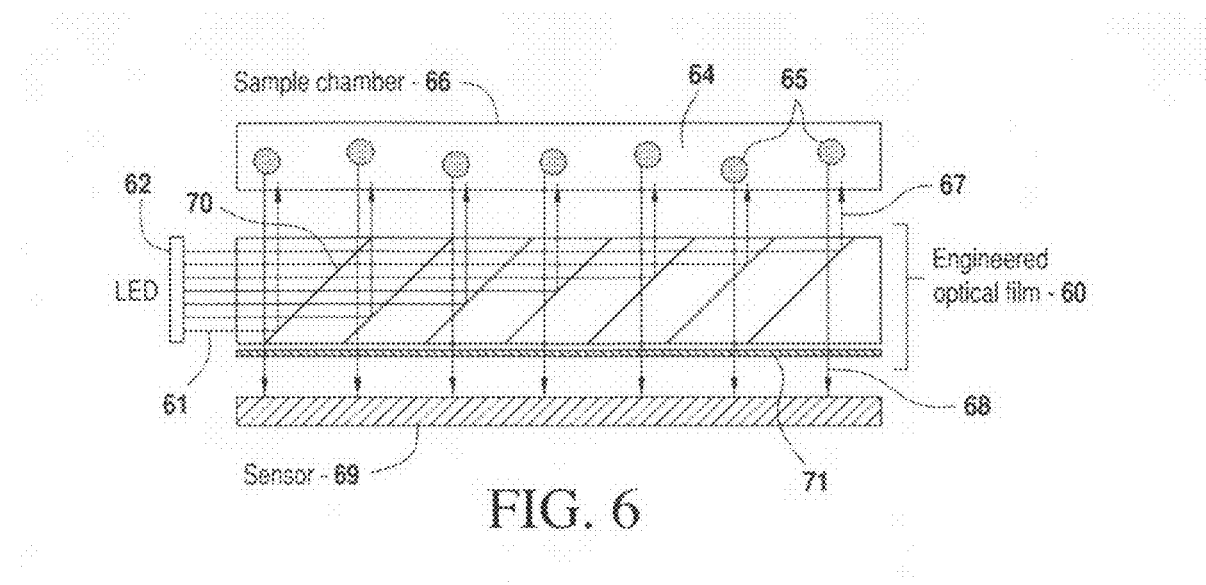
FIG. 6 is a simplified schematic diagram of yet another miniaturized embodiment of an exemplary optical diagnostic assay apparatus as part of the present invention.

Yet another embodiment of an optical diagnostic assay apparatus suitable for usage as part of the present invention is illustrated in FIG. 6. A thin film optical component (an engineered optical film) 60 directs excitation radiation 61 from an LED 62 onto a sample 64 and analytes 65 captured therein within a sample chamber or reservoir 66. The optical component 60 acts as a dichroic filter to direct short wavelength radiation 67 of the excitation radiation to the sample chamber 66 positioned at one side of the film while concurrently allowing only longer wavelength radiation 68 emitted from fluorescent reporters attached to the analytes 65 to pass in the opposite direction through the optical component to a sensor 69. The Figure schematically depicts this exemplary embodiment in which the optical film 60 is engineered to possess both dichroic (depicted as slanted lines 70) and bandpass (depicted as horizontal line 71) properties, so as to realize a compact fluorescence detection system to excite and assess fluorescently labeled target cells, particulates, or reservoirs of chemical or biological analytes. In an alternative embodiment, the optical film may be engineered to possess only dichroic functionality. The manner in which optical films may be engineered to provide such characteristics is known, such as described in *Thin-Film Optical Filters*, Fourth Edition (Series in Optics and Optoelectronics), H. A. Macleod, CRC Press, ISBN-10: 1420073028 (2010), for example.

Figure 7:
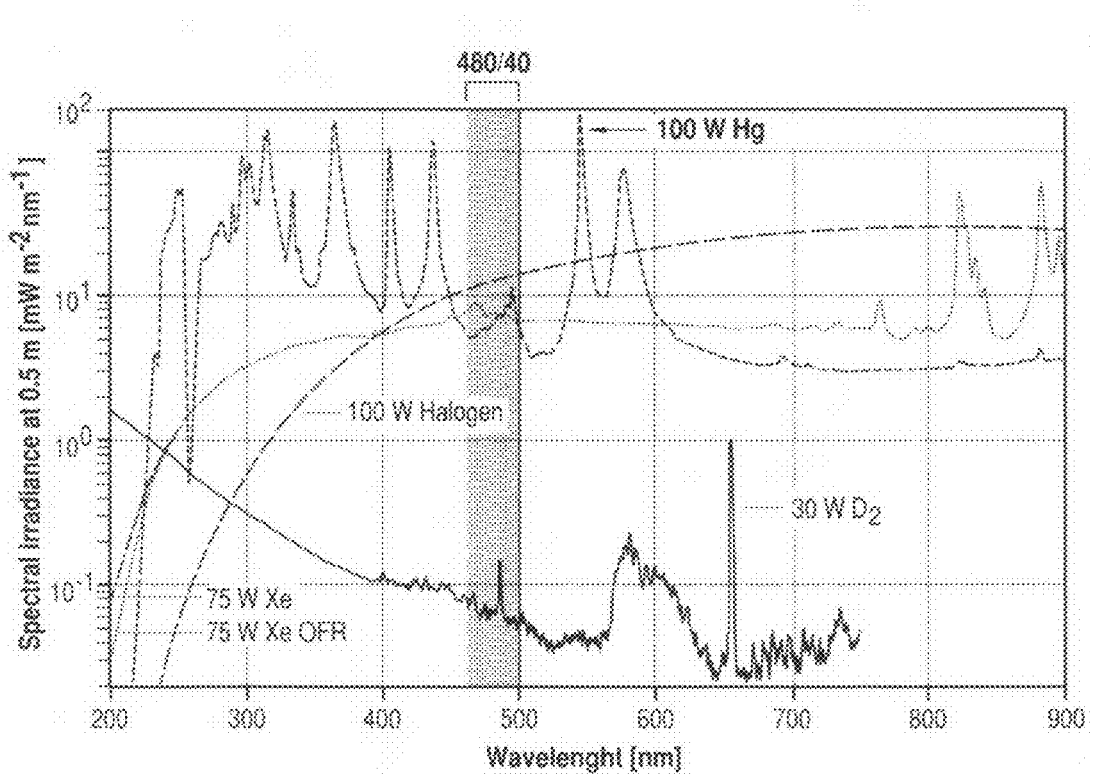
FIG. 7 is a graph of spectral radiance power versus wavelength for various light sources.

FIG. 7 is a graph denoting the spectral output radiation of a typical 100 watts (W) short arc mercury (Hg) source, such as is commonly used to excite fluorescent reporter elements in prior art optical assay systems. The Figure illustrates that for Hg short arc source input power consumption of 100 W, only about 0.1 W of total radiation in the 460-500 nm band is produced for FITC (fluorescein isothiocyanate) excitation, according to the uppermost curve (indicated with the arrow). This represents about 0.1% luminous efficiency, in comparison to the input power and total radiation of an exemplary LED with luminous efficiencies above 10% and approaching 50%, preferred for use as the light source(s) in the various embodiments of the optical assay portion of the invention.

Figure 8:
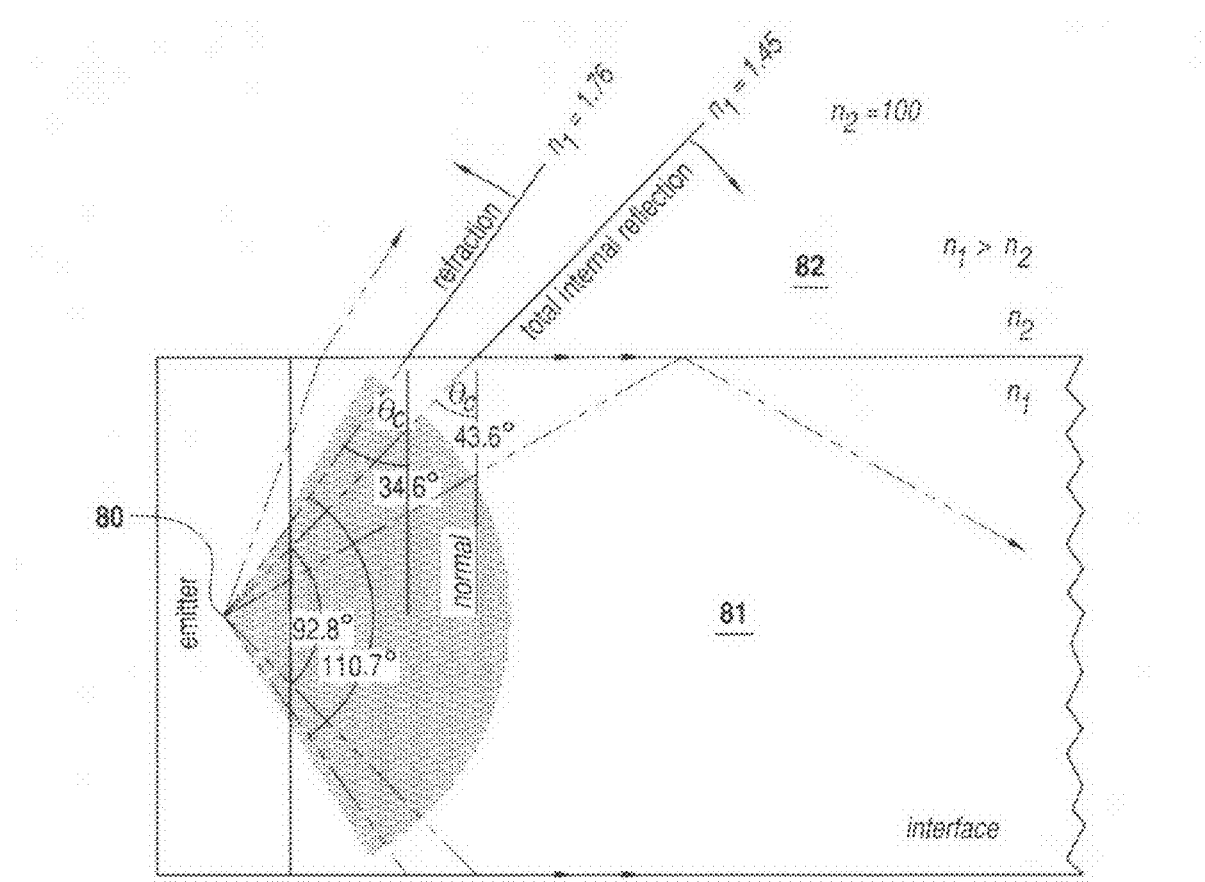
FIG. 8 illustrates the critical angle of incidence required to achieve total internal reflection within an optical waveguide of particular refractive index at an air interface.

FIG. 8 illustrates the critical angle of incidence required to achieve total internal reflection of radiation from an emitter (shown as an idealized point source 80) within an optical waveguide 81 having a refractive index $n_1$ of between 1.45 and 1.76, at an air interface where air 82 has a refractive index of $n_2=1.00$. As shown in the Figure, a narrow viewing angle emitter is needed in order to promote total internal reflection within the waveguide. In this configuration and indicated refractive indices, light emitted beyond a viewing angle of 92.8° to 110.7° is refracted and, thus, lost. But light emitted by a small dimension LED 80 with a narrow viewing angle, equal to or less than approximately 90°, is reflected within the waveguide. Hence, an optical assay apparatus (preferably of microminiature size) having components selected with these characteristics is effective to promote light retention within the waveguide.

Figure 9:
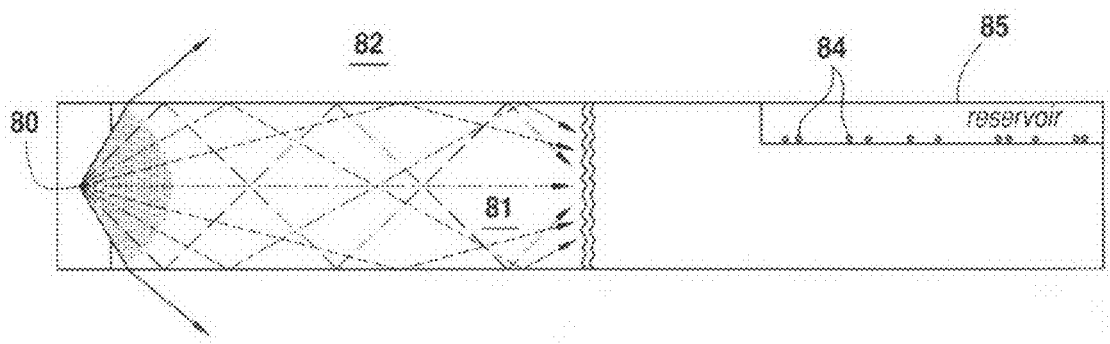
FIG. 9 is a simplified diagram of an optical waveguide cartridge having a reservoir containing a sample to be assayed, illustrating total internal reflection of the excitation radiation within the cartridge for efficient direction thereof onto the sample.

FIG. 9 depicts the use of a cartridge comprising a combination waveguide/sample reservoir to efficiently direct excitation light from the emitter to the sample contained in the reservoir. In the Figure, emitter 80 (a side-emitting source such as an LED) emits excitation radiation in a predetermined band (utilizing appropriate bandpass filtration, as necessary) according to the nature of the reporter elements bound to analytes 84 in a sample undergoing assay within a reservoir 85. Emitter 80 is optically coupled to an optical waveguide 81, which is surrounded by air 82. Excitation radiation entering the waveguide at appropriate angles to achieve total internal reflection is reflected within the waveguide body and directed to the sample within the reservoir 85 of the cartridge. Operation is analogous to that described for the embodiments of FIGS. 5 and 6.

The fluorescent reporters utilized in current standard fluorescence-based assay methods are generally linked to various recognition elements that interact with or bind to specific target analytes or classes of analytes to form labels for staining cells, tissues, or other samples for fluorescent imaging and spectroscopic analysis. Fluorescent reporters include small organic molecules such as fluorescein isothiocyanate (FITC), rhodamine and its derivatives, or members of the cyanine dye family; nanocrystal reporters such as quantum dots; or fluorescent proteins such as Allophycocyanin (APC), R-phycoerythrin (RPE), Peridinin Chlorophyll (PerCP), or Green Fluorescent Protein (GFP). Recognition elements include antibodies, nucleic acids and other ligands.

The fluorescent reporter and target recognition and elements of certain labels, although linked, function separately. The fluorescence properties exhibited by such labels can be independent of analyte binding, and errant detection of free, unbound label can result in ambiguous or misleading fluorescence data. Thus, it is often necessary to separate or otherwise differentiate label-analyte complex from unbound label. Typical sample labeling methods involve combining fluorochrome-linked labels that have a binding affinity for a particular target analyte with a sample and reacting under conditions that facilitate binding of the target analyte (if present in the sample) to the label. A wash step to remove unbound label typically follows. Finally, the fluorescence, opacity to light or other radiation, or other physical properties of the labeled sample are assessed and used to identify and/or quantify the label-analyte complex.

Other fluorescent-labeling approaches employ labels that possess fluorescence properties that differ upon binding to, activation by, or other interaction with a target analyte. Such homogeneous, no-wash, one-step, or single-pot assay chemistries can include some small organic molecules; a fluorphore-quencher fluorescence resonance energy transfer (FRET) or other proximity pair; or those based on enzymatic conversion of a non-florescent substrate into a fluorescent product. Specific examples of small molecule reporters that do not require removal of unbound or unreacted label include the cyanine dimers (YOYO-1, TOTO-1, JOJO-1, for example), which are effectively non-fluorescent in the absence of nucleic acids but exhibit up to 1000-fold fluorescence enhancement upon DNA binding; DAPI (4',6-diamidino-2-phenylindole), which exhibits an approximately 20-fold fluorescence enhancement upon binding to the minor groove of dsDNA; and calcein AM, a membrane-permeant acetomethoxy derivate of calcein that is cleaved by esterases in live cells to yield cytoplasmic green fluorescence, and that can be applied to various cell viability assays.

An example of a FRET-based homogenous label is the so called molecular beacon oligonucleotide hybridization probes that comprise an 18-30 base pair "loop" region complementary to a target sequence, a "stem" formed by the attachment to both termini of the loop two short (5- to 7-mer) oligonucleotides that are mutually complementary, a covalently attached 5' fluorophore, and a covalently attached, non-fluorescent 3' quencher. When the beacon is not bound to its target sequence, the loop is held in a closed shape by complementary binding of the stem sequences, the fluorophore is held in proximity to the quencher, and any fluorescent emission from the label is quenched. Upon binding to a target sequence, the beacon unfolds, the fluorophore is distantiated from the quencher, and illumination of the label with excitation light results in fluorescence emission. Thus, the emission report is hybridization-dependent and only occurs if the target nucleic acid sequence is present in the test sample, thereby eliminating the necessity of a wash step to remove unbound fluorescent label.

Exemplary enzyme-based homogenous fluorescence approaches include those employing Rhodamine 110 (R110) fluorophore-peptide conjugate substrates in which covalent linking of peptides to amino groups on R110 suppresses its fluorescence. These peptides are cleaved by target enzymes, converting the conjugate to a fluorescent monoamide, and then to R110, with an additional increase in fluorescence. The fluorescence yield is in proportion to the abundance and/or activation of the target enzyme, and quantitative determinations of a given enzyme can be performed. Such enzyme-labile fluorescent substrates can be used to continuously measure enzyme activity in vitro, and they have been applied to assays for apoptosis-related proteases such as caspase-3, and blood associated serine proteases including thrombin and plasmin.

Fluorescence-based methods such as fluorescent-assisted microscopy (FAM) can be applied to improve detection and diagnosis of diseases such as malaria or tuberculosis, for example. Microscopic examination of stained specimens is an early established method for detecting malaria and tubercle bacillus, and it remains a gold-standard diagnostic procedure. *Plasmodium* protists are visible as foreign nuclei within the erythrocytes of a malaria-infected host. The *Mycobacterium* causative agents of tuberculosis are "acid-fast," i.e., once stained with a basic fuchsin dye, they are difficult to decolorize, and retain their stained color even when treated with a mixture of acid and alcohol. Staining for this characteristic facilitates early presumptive diagnosis and enumeration of acid-fast bacilli present in a biological sample. Fluorescent dyes Auramine O and rhodamine B bind to mycolic acids in the mycobacterial cell wall, unbound dye can be removed using acid-alcohol decolorizer solution, and potassium permanganate can be employed to suppress nonspecific background fluorescence.

Implementation of a fluorescent label such as a fluorescence in situ hybridization (FISH) probe, fluorescent nucleic acid label to stain parasite DNA, fluorescent acid-fast stain such as auramine O or auramine-rhodamine, or fluorophore-conjugated antibody against parasite or mycobacterial specific antigens can be used to label a blood or other patient sample to enhance the capacity to identify and enumerate, for example, parasites or pathogens, thereby increasing assay overall selectivity and sensitivity. Fluorescence microscopy offers many advantages over classic methods for detecting *Plasmodium, Mycobacterium*, and other pathogens because of its speed and simplicity, the ease of directly examining slides, and the reliability and superiority of the approach. In some cases, such fluorescence-based pathogen labels can be prefilled into assay cartridges and dried or otherwise stored for later use.

In an exemplary embodiment, the sample holder includes a planar substrate configured to contain one or more solid state excitation sources, and additionally configured to exploit the intrinsic elastic deformability of the substrate to ensure close, low optical loss mechanical coupling between the analyte-containing sample cartridge and the fluorescence excitation source. In certain other embodiments, the fluorescence readout and detection system is implemented such that one or more sample reservoirs, one or more solid state radiation sources, power supply or other energy storage device, and a switch to selectively interrupt or direct electrical power from the energy source to one or more of the said radiation sources, are integral to a single, common substrate or package.

The source(s) are optically coupled to the sample reservoir(s) and thereby used to excite fluorescent reporter elements contained within the sample(s). In certain embodiments suitable for the optical assay components portion of the invention, the fluorescence readout and detection system are implemented such that the sample containing cartridge and the reader are configured to be complementarily disposed such that the functioning of the reader and/or the identity of the cartridge is dependent on one more or prescribed pairings. In certain embodiments, one or more bandpass filters are configured to restrict transmission of excitation wavelengths from the sample reservoir while allowing passage of fluorescence emission wavelengths from the sample reservoir. These bandpass emission filter(s) may be integral to the cartridge, holder, or both. In certain embodiments, a side-emitting radiation source such as an LED may be coupled to a sample-containing cartridge such that radiation entering the cartridge at appropriate angles is reflected within the cartridge body and directed to the sample within the reservoir of the cartridge. In other embodiments, the geometry of the radiation source and/or the angle of luminous flux of the radiation source are implemented to maximize total internal reflection or otherwise provide efficient optical coupling between the source and the sample.

Figure 10A:
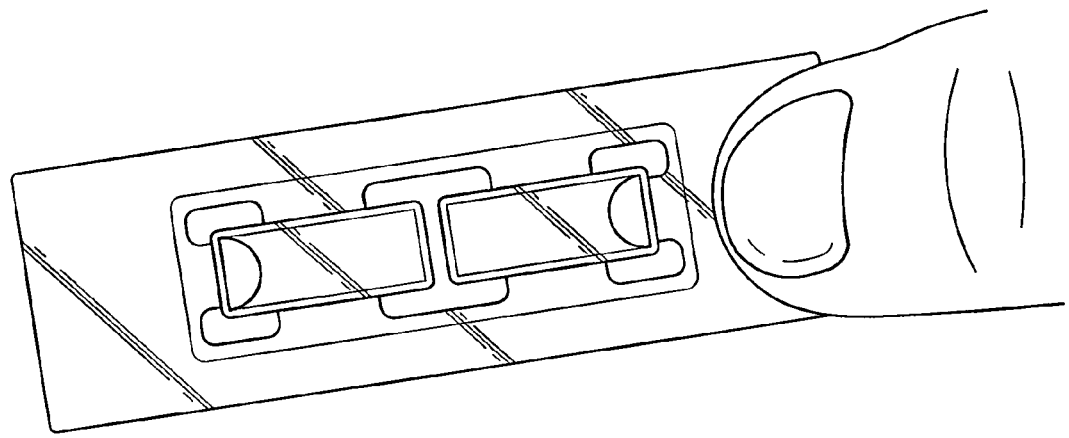
FIGS. 10A and 10B are respectively a photograph and a representative drawing thereof of a prototype of an apparatus utilizing certain principles of the invention wherein the excitation radiation source and the sample-containing reservoir are integrated together.
Figure 10B:
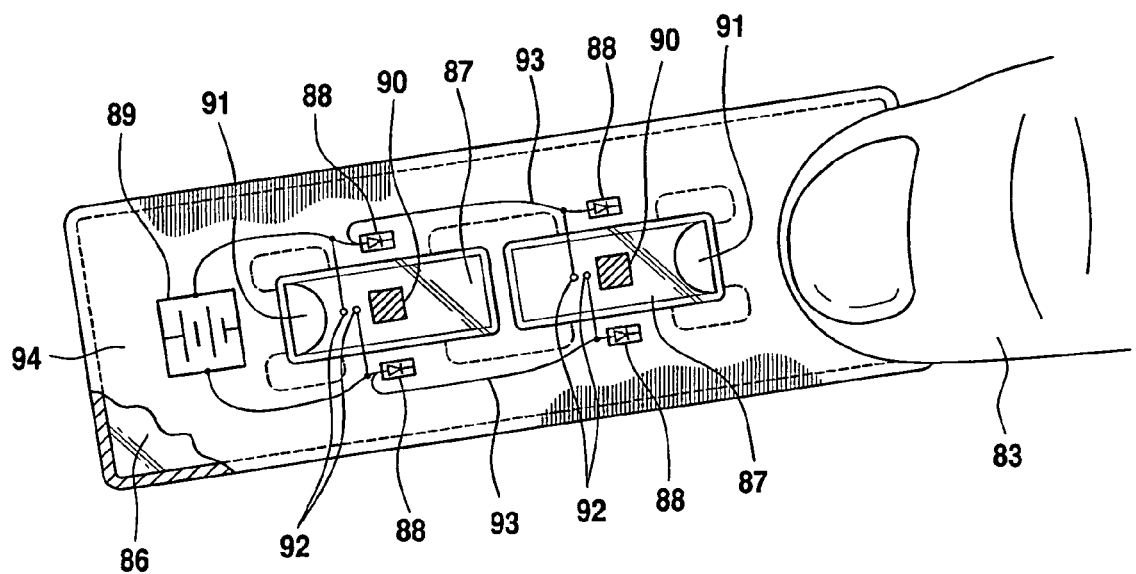

FIG. 10A is a photograph, and FIG. 10B is a drawing (for purposes of clarification) illustrating an enlargement of the component configuration within the case shown in the photograph, of a prototype apparatus utilizing principles of the invention for miniaturization of the optical assay portion. In FIG. 10B, a double-ended configuration has the excitation radiation source (two pairs of light-emitting diodes (LEDs) 88) integrated with the sample reservoir 87 (two, at opposite ends of a cartridge 94), i.e., self-contained within the cartridge. This demonstrates the compactness of the apparatus that enables it to be coupled in a handheld arrangement. Approximate size is illustrated in both Figures by the thumb 83 of the individual holding the cartridge. All components of this apparatus are mounted on a substrate 86 encompassed in principal part by cartridge 94. An opening in the cartridge shown by a dotted line at mid-figure in FIG. 10B, and somewhat more clearly in FIG. 10A, reveals the pair of reservoirs 87 and a sample inlet 91 in each. In this embodiment of optical assay apparatus, the battery 89 or other power supply may be a rechargeable or non-rechargeable electrochemical cell such as a nickel-metal hydride, lithium-ion (polymer), or alkaline battery; an electrical energy storage device such as an electric double-layer capacitor (EDLC) or supercapacitor; or other high energy density storage device such as a surface-mediated cell (SMC). Electrical leads 93 connect the battery 89 to the LEDs 88.

A sample of material to be assayed is loaded through inlet 91 into reservoir 87, after labeling the sample with a reporter element designed to attach to analytes of interest in the sample. The sample or a suitable portion thereof is positioned in a counting area 90 of the reservoir 87 for optical exposure to the LEDs 88 mounted at either side of the respective reservoir. Fluid-sensing switches 92 are arranged to monitor passage of the sample material from the inlet to the counting area. The reporter element attached to analytes in the sample is adapted to emit an optical signal in response to irradiation of the sample with light in a predetermined bandwidth from the LED(s). These optical signals are captured by an image sensor (not shown), and data contained in this captured optical information is analyzed for purposes of the assay.

Figure 11:
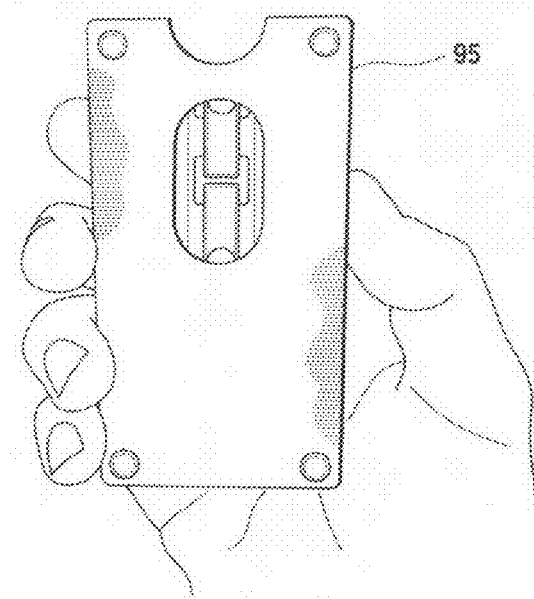
FIG. 11 is a photograph of another prototype of a fluorescence readout and detection system as a handheld assay apparatus, utilizing principles of the present invention.

The detection system may be implemented using the image sensor conventionally integral in a mobile electronic device such as a smartphone, laptop or tablet computer, or digital camera, that enables portability of the overall apparatus. In any event, the detection system is preferably in functional communication with one or more devices for processing detector data. Power efficient and adept configuration enable realization of a fluorescence readout and detection system as a handheld or otherwise especially compact apparatus(es) in certain embodiments, such as the apparatus 95 shown in the photograph of FIG. 11.

Figure 12B:
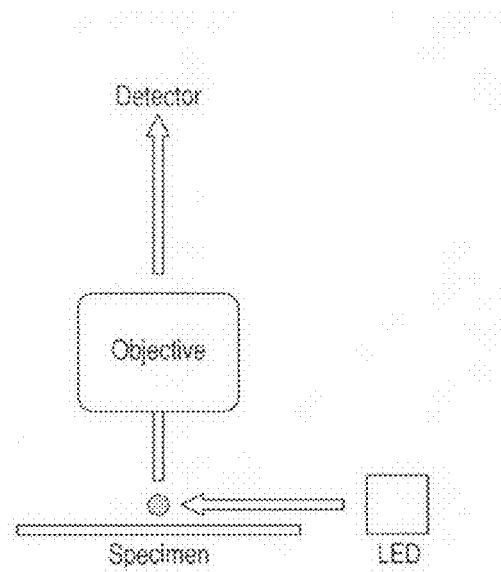
FIG. 12A is a photograph of the handheld assay apparatus of FIG. 11, constructed according to the inventive scheme/principles of excitation and detection of FIGS. 3A, 3B, with the logistical arrangement of optical assay elements of FIG. 12B.
Figure 12A:
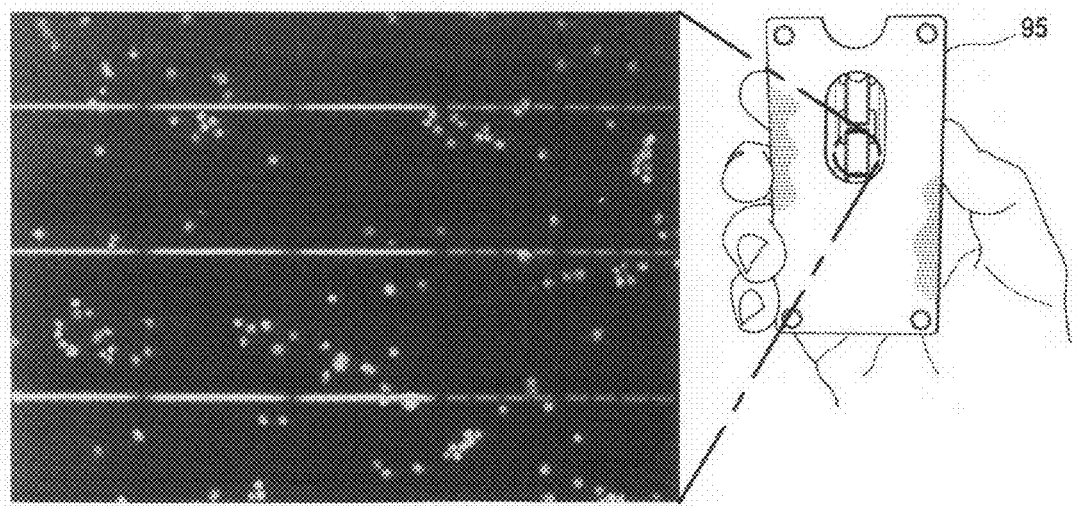

To perform a diagnostic assay, specimens or samples to be assayed may be introduced into cartridges that are prefilled with labeling reagents for interaction with analytes of interest, and the cartridges containing these in situ labeled samples may be loaded into a fluorescent reader for subsequent microscopic or other analysis. The fluorescence detection system may be implemented using a cartridge and holder format. Such a system is shown as fluorescent assay reader apparatus 95 (FIG. 12A, corresponding to that in FIG. 11), which includes one or more solid state radiation sources (e.g., LED(s)), a power supply such as a battery or other energy storage device, and a switch to selectively interrupt or direct electrical power from the energy source to one or more of the radiation sources, of a size that enables the apparatus 95 to be handheld (and thus, completely portable). The apparatus utilizes the excitation scheme of FIG. 3A together with the LED-specimen-objective-detector arrangement illustrated in the simplified schematic diagram of FIG. 12B. Samples to be assayed for fluorescently-labeled analytes of interest or other suitable reporter elements are loaded into one or more sample reservoirs in a cartridge apparatus (such as illustrated in FIG. 9), which may be distinct from the holder. The cartridge may have its own radiation (i.e., light-emitting) sources, or joined with the holder having such source(s) mounted thereon, so as to direct the radiation onto the sample in the reservoir and thereby excite particular fluorescent reporter elements attached to analytes contained within the sample(s). The enlarged image of the display shown in FIG. 12A is of nucleated mammalian cells labeled with green-fluorescent dye SYTO13, obtained according to the scheme of FIGS. 3A and 12B.

Alternative to the types of power supply noted above, solar power may be used to charge the energy storage source or to directly power the excitation radiation source of the apparatus. Another alternative is to charge or power the energy source via an inductive mechanism. Or a carbon-nanotube-based battery with an approximate ten-fold increase in volumetric and gravimetric energy density compared to conventional storage devices may be employed to power the solid state fluorescence excitation source. Configurations of high luminous efficiency solid-state fluorescence excitation sources; source emission wavelengths matched to fluorescent reporter element absorption (excitation) peaks; efficient optical coupling of excitation sources to fluorescent reporter element containing samples; and improved, high volumetric and/or gravimetric energy density energy storage devices to power the excitation sources enable fluorescence readout and detection systems to be realized in certain embodiments as a disposable, hand-held or otherwise especially low-cost and compact apparatus(es).

According to certain aspects of the invention, fluorescent reporter elements or labels may be preloaded into the sample reservoir(s) such that they bind to or are otherwise activated by subsequent loading of an aliquot of the sample(s) to be assayed into the sample reservoir(s). Such labels can be dried, lyophilized, or otherwise stabilized such that said labels are able to be stored for months or years before being combined with samples being assayed. Furthermore, different labels may be arrayed in various sample reservoirs, in different spatial regions of a single reservoir or multiple reservoirs, or combined in other ways to enable multiple parallel or simultaneous assays to be performed on a given sample or group of samples.

According to another aspect of the invention, an electrical circuit may be configured within the fluorescence detection system such that upon being loaded into the sample reservoir, a fluidic sample serves to conduct an electrical current that indicates the sample has been loaded, and which activates or otherwise switches on the solid state fluorescence excitation source(s).

According to yet another aspect of the invention, the switch that opens and closes the electrical circuit between the fluorescence excitation source and the power source of the compact apparatus is configured as a tape, ribbon, or dielectric film for selectively interrupting the circuit, and which may be manually manipulated to complete or open the electrical circuit. Together these elements may yield orders of magnitude improvement in overall system luminous efficiency and provide compact, low-power, portable, reduced cost, and even disposable fluorescence readout and detection systems.

FIGS. 13A, 13B and 13C constitute a simplified exploded perspective view of a preferred embodiment of apparatus of the invention, in which the miniaturized optical assay components are combined with a conventional mobile electronic device to enable portability; selective assay data storage, manipulation, comparison and transmission; fluorescence detection utilizing the device image sensor; assay imagery and function control on the device screen; powering of the fluorescence detection system from the device battery or other source of electrical energy; and other advantages. FIG. 13A illustrates a simplified perspective view of a conventional stand-alone smartphone, taken from the back of the device with a showing of the bottom and one side along with the back of the smartphone case; FIG. 13B illustrates a coupler, frame, or support structure for combining the smartphone and an optical assay portion into an assembly or apparatus; and FIG. 13C illustrates the optical assay portion and the smartphone coupled together synergistically in compact portable form for use in performing optical assays according to the invention.

Wireless cell phones or mobile phones of a size that permitted them to be handheld and carried, albeit initially rather bulky, became popular in the 1980's. But in that era, the phone was virtually strictly a telephone, that is, its use was substantially limited to making and receiving telephone calls. With what is now the typical rapid progress of technology, the mobile phone evolved into an electronic device capable not only of phone service, but of performing or providing numerous other functions and features. These include exchange of text messages, emailing, GPS (global positioning system) navigation and associated location of places of interest, maps, music and other information downloads, appointment scheduling, news and magazine readership, photography, electronic game playing, voice recognition and response, weather reporting, and numerous other capabilities provided to the user. Perhaps one of the most significant features of the mobile phone is its capability to download and utilize thousands of applications, or "apps," from a library of apps typically maintained by the device manufacturer or licensor but that may be designed by hundreds or thousands of private software designers as well as by the manufacturers and licensors, and available from the internet or the cloud.

As a consequence of this technical evolution, mobile phones have come to be characterized as "smartphones" (or smart phones), an appellation that recognizes the built-in and downloadable program intelligence of the device owing to internal microcomputer, microcontroller or microprocessor as well as internal digital data memory such as RAM and ROM, image sensing for photography, receiver and transmitter, and a wide variety of ancillary functions including audio recording, music playing, and so forth. These devices include iPHONE® smartphones, ANDROID®-based smartphones, WINDOWS® smartphones, and BLACKBERRY® smartphones (marks designated with the superscript symbol ® are registered trademarks of their respective owners for the respective products generically listed immediately following the respective appearances of the marks), among others. Except for the fact that the device retains its capability of use for making and receiving phone calls as its primary feature (or at least among its primary features), it might lose the nomenclature of "phone." Indeed, for a period of time and perhaps still, some devices of this type are referred to as "personal assistants," in recognition that they possess the capabilities noted above such that they are similar to persons relied upon by their superiors (in the environment of the workplace) to provide such assistance. It is important to emphasize that although the terminology "smartphone" is used throughout this specification, the description of the embodiments and methods of the invention are applicable as well to any relatively compact mobile electronic device possessing the characteristics and features utilized in those embodiments and methods, and such devices are intended to be encompassed by that terminology. These other mobile electronic devices might include tablet computers such as the iPAD®, laptop computers such as PCs or the MACBOOK AIR® (marks designated with the superscript symbol ® are registered trademarks of their respective owners for the respective devices listed immediately preceding their marks), appropriately featured digital cameras, for example, and other such devices. The smartphone is preferred for use in the synergistic combination with an optical assay system because it constitutes a simple, economical, compact, efficient and ready-to-use partner thereof.

The smartphone 110 depicted in FIG. 13A is ubiquitous in the sense of being an artificial representation of virtually all conventional devices of this type, possessing a compilation of the features of compactness, portability (i.e., mobility, in the sense of adapted to be carried about easily, with comparatively little or no measurable physical exertion), battery or other energy source operation, camera, lens(es), wireless data transmission/reception, digital data memory (including but not limited to data storage media or memory that allows manipulation, such as RAM). As viewed in perspective toward its back 111a, also revealing its bottom 111b and one side 111d, smartphone 110 has an electrical socket, receptacle or female connector 112 located at the bottom 111b of its case 111. The connector 112 is fitted in a conventional manner with electrical contacts (not shown) and is configured to accept an electrical plug (male connector) 116 (FIG. 13B) with contacts arranged and adapted to mate with those of the connector 112 so as to permit power transfer and data transmission between the smartphone 110 and apparatus to which connector 116 is electrically connected.

A camera integral with the conventional smartphone 110 includes a lens 113 exposed on and secured to case 111, and internal conventional components including image sensor and automatic focusing for enabling photography to be performed with the phone. The location of camera lens 113 shown in the smartphone depicted in FIG. 13A is midway between the sides 111c and 111d of the case 111 at the upper part of its back 111a. It is to be understood, however, that the actual location is immaterial to the essence of the present invention. As will be clear from the description to follow, lens 113 may be positioned at other points on the case according to the design of the particular smartphone supplier, without impacting the nature, function or method of the invention. An LED (not shown) associated with the lens 113 to provide a flash when the smartphone camera is activated (clicked) under low ambient light conditions is preferably disabled (by a control actuatable or programmable from the smartphone) to prevent it from affecting the reading or results of the optical assay.

Referring now to FIG. 13B, an adjunct structure according to a preferred embodiment of the invention includes a coupler 115, preferably composed of clear relatively hard plastic, fabricated to slide (i.e., to be slid) over the case 111 of the smartphone 110. The coupler 115 is open at one end 115a to allow it to be slid over the bottom end 111b of the smartphone in such a way that when the coupler is completely fitted, preferably with a snug fit, onto the phone, a male electrical connector 116 affixed to and projecting internally of the coupler at the closed bottom end 115b of the coupler will engage and mate with the female electrical connector 112 on the bottom end 111b of the phone to form an overall electrical connector 119. Preferably, connector 116 is configured with female function externally to allow the coupled assembly to be charged or externally powered. The mating of conventionally configured electrical contacts (not shown) of connectors 116 and 112 enables a transfer of power from the phone's battery through connector 119 and electrical leads 117a, 117b running within the sides 115c, 115d of the coupler to one or more LEDs 120, 121.

The LEDs are fixedly positioned in predetermined locations at either one or both side(s) 118a, 118b of a receptacle 118 fabricated as an integral part of coupler 115. The receptacle is integral with the upper surface (in the exemplary orientation illustrated in the Figure) of coupler 115, above the open end 115a and midway between the sides 115c, 115d thereof. If desired, only one LED (e.g., 120) with associated lead (117a) may be utilized (thereby making a second LED (121) and its associated lead (117b) unnecessary, or the two LEDs may be fabricated and selectively activated to generate different light wavelength bands in the performance of optical diagnostic assays. The open end 115a and general overall shape of receptacle 118 are configured to receive a cartridge 122, a hemocytometer, for example, in a relatively snug fit intended to secure it in a firm position therein (discussed with reference to FIG. 13C, below). Receptacle 118 may have a bottom surface formed by the upper surface of coupler 115, or, because the hemocytometer is not inserted into the receptacle until the smartphone 110 is in place in coupler 115, may be open at its bottom such that the back 111a of the smartphone's case 111 is utilized to support the hemocytometer thereon.

Referring now to FIG. 13C, cartridge 122 may be of any of the miniaturized types described above, preferably as shown in FIG. 4, 5 or 6. The cartridge 122 illustrated in FIG. 13C is fabricated to have a pair of sample reservoirs or cell counting chambers 124, 125 fixedly retained in a transparent (optically clear) substrate, which allows the cartridge to be inserted from either end such that a selected one of the two reservoirs is located within the receptacle 118 for the optical assay of a sample loaded therein. Alternatively, the cartridge may be fabricated with only a single reservoir 124 available to be disposed within receptacle 118. The two-reservoir embodiment is allows two different samples to be pre-loaded and more quickly assayed. Also, the use of two LEDs 120, 121 allows the two different samples to be exposed to excitation light of different bandwidths according to the analyte sought to be detected (and counted). In any event, the configuration and size of the receptacle 118 and the cartridge 122 are predetermined to assure that when the cartridge is fully inserted into the receptacle, the sample reservoir (e.g., 124) is positioned directly over the lens 113 of the smartphone camera and along an axis through the two LEDs.

Optical assays are performed in a manner described earlier herein. For example, a sample specimen of blood from a subject (human or animal) under observation is pre-loaded into chamber 124 (which may be a support for the sample in contrast with a volumetric retainer). After a hemocytometer cartridge containing the sample(s) is inserted into receptacle 118, and with the smartphone 110 "on" (activated), the camera icon on the touchscreen of the smartphone may be touched to cause the opening of lens 113 and simultaneous activation of LED 120, whereby the excited fluorophores (reporter elements) attached to the cells undergo fluorescence to produce optical signals representative of content of analytes of interest, to be captured as optical information by the device's image sensor. Other methods of activating the camera function of the smartphone are described below.

FIG. 13D illustrates an alternative scheme for electrically connecting an optical assay cartridge 122 to the device (e.g., smartphone) battery via the coupler 115. Here, the cartridge 122 is fabricated to include its own LEDs, such as described above with reference to FIGS. 10A and 10B, and is provided with an electrical connector 123 to mate with an electrical connector 127 of the receptacle 118, when the cartridge is fully inserted into the receptacle. An electrical cable 128 has leads connected to contacts in connector 127 and in connector 116 of coupler 115 to provide battery power from the device to the cartridge (i.e., to its LEDs) when the cartridge is fully inserted in the receptacle and the circuit between the smartphone and the cartridge is closed (activated). This arrangement may be used in place of LEDs 120, 121 mounted on the coupler itself.

An open bottom of receptacle 118 (i.e., so that the cartridge is supported by the back 111a of the smartphone case 111) assists in assuring an absence of intervening interference between emissions from the sample and the opened camera lens, as might occur, albeit unlikely, with a clear plastic bottom plate on the receptacle. The resulting image thereof (i.e., optical information regarding cells (or other analytes) that have been labeled, for example, as antibodies, seen as a particular color) is captured by the image sensor of the camera and retained in storage media therein (internal memory) to allow the results of the assay to be viewed on the smartphone display screen immediately (or later, upon retrieval from memory). In addition, the digital data constituting the assay results may be selectively transmitted from the smartphone to a remote site, such as to an electronic records storage location (HM7 patient files, for example) for the particular subject under observation. The intrinsic software of the smartphone is utilized in performing the assay, and one or more applications (apps) such as the NIH imaging program (designated "Image") may be downloaded to enable comparison against the assay. Recharging of the smartphone battery may be accomplished in the usual manner, as needed, either by removing the smartphone from the coupler (or, if mated connector 119 is configured as described above, to allow insertion of the charger lead into the connector 119) to re-energize it for further assays.

FIG. 14 illustrates the front 111e of conventional smartphone 110 with the coupler 115 in place and its overlying flange 115e maintaining the coupler on the smartphone without blocking any portion of the smartphone's typical screen (display) 130. By way of example, a pair of different apps 131, 132 is displayed on the screen, having been downloaded from the internet or the cloud to the smartphone. The number of apps displayed at any given time depends on the number downloaded and available to be brought up by the user (e.g., a person conducting the assay). Any one or more apps may be selected, such as NIH Image program, according to the desired analysis of the sample in the diagnostic chamber (e.g., 124). Smartphone operation may be controlled using its actual alphanumeric keypad (such as is available on the Blackberry® phone and certain others, not shown) or its virtual keypad 135 brought up on its touchscreen 130, or by touching appropriate icons on the smartphone screen, depending on the type, functions and features of the particular smartphone being used.

In FIG. 15, an alternative embodiment of a coupler 138 used for coupling a smartphone 139 and an optical assay system (the cartridge of that system not shown in this Figure) comprises a specially designed back plate 141 of the smartphone case 140. Because this alternative requires a special case or at least a special removable/replaceable back plate, which departs from use of a standard commercially available smartphone, it is less preferred than the type of coupler 115 described with reference to FIGS. 13 and 14. In the alternative embodiment of FIG. 15, back plate 141 is composed generally of the same material as the rest of the case 140. The lens 143 of the integral image sensor of the smartphone is covered by a clear relatively hard plastic receptacle 145 incorporated in the back plate 141, but otherwise substantially similar in design and location to the receptacle 118 of FIG. 13B.

Receptacle 145 has an open end 145a to allow insertion of a sample cartridge with snug fit, and a clear plastic base 145b overlying the camera lens 143 to support the cartridge with its diagnostic reservoir, chamber or sample support positioned directly over the lens. As with receptacle 118, the receptacle 145 has one or a pair of LEDs 147, 148 affixed at opposite sides thereof, in alignment with the chamber containing the sample to be assayed when the cartridge is in place in the receptacle. This assumes, of course, that the cartridge itself is not outfitted with internal LEDs as described above, that would obviate a need for the receptacle mounted light sources. Electrical leads 150, 151 connected to the respective LEDs 147, 148 run along the interior underside of backplate 141, which preferably extends over the bottom 153 of the smartphone 139. To provide an electrical connection to these leads so as to supply battery power to the LED(s), the smartphone's electrical connector 154 may be modified to include electrical contacts "hardwired" to leads 150, 151, beyond its conventional contacts.

Figure 16:
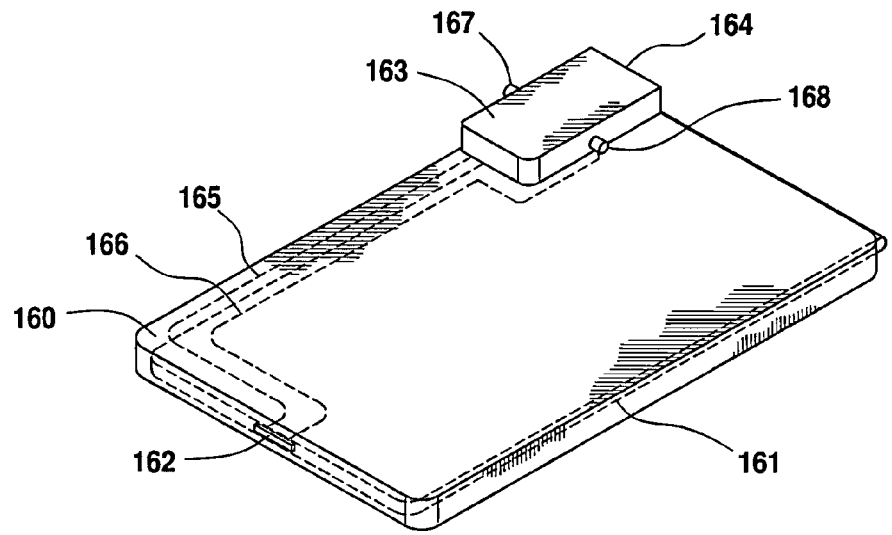
FIG. 16 is a simplified partial perspective view of the back of a tablet computer with a coupler assembled thereto, according to another alternative embodiment of the invention.

FIG. 16 is a simplified perspective view of the back of a tablet computer 161 with a coupler 160 slidably assembled thereon, according to an embodiment of the invention utilizing a different mobile electronic device from the smartphone. The coupler 160 is preferably composed of transparent hard plastic material adapted to receive the tablet 161 in a snug fit therewith, and to concurrently cause mating of an electrical connector 162 on the coupler with the conventional electrical connector (hidden beneath connector 162) of the tablet. The tablet connector is fitted with contacts or pins connected to the tablet battery as well as to various internal electronic components of the tablet providing its computer, controller, data storage, image sensor and data transmission functions, and for exchange of data. Electrical leads 165, 166 within the wall of the coupler connect the battery of the tablet via the tablet connector and coupler connector 162 mated therewith to a pair of LEDs 167, 168 at either side of a receptacle 163 of the frame. Here again, an LED-fitted sample cartridge and mating electrical connectors on the cartridge and the receptacle 163 would provide an alternative to light source(s) mounted on the receptacle of the coupler.

With the frame in place on the tablet, the back of the tablet is positioned to place its image sensor lens in optically coupled configuration with the reservoir of the assay apparatus portion. To that end, the receptacle 163 of the frame 160 is positioned to have a cartridge of the assay apparatus inserted into the opening 164 therein such that a sample of material to be assayed is positioned in its reservoir directly over the image sensor lens and optically coupled to the LEDs 167, 168 at either side thereof. Operation of the compact portable optical assay apparatus of FIG. 16 corresponds to that described above for the smartphone embodiments, the only difference being that in this example the mobile electronic device is a tablet computer.

Figure 17:
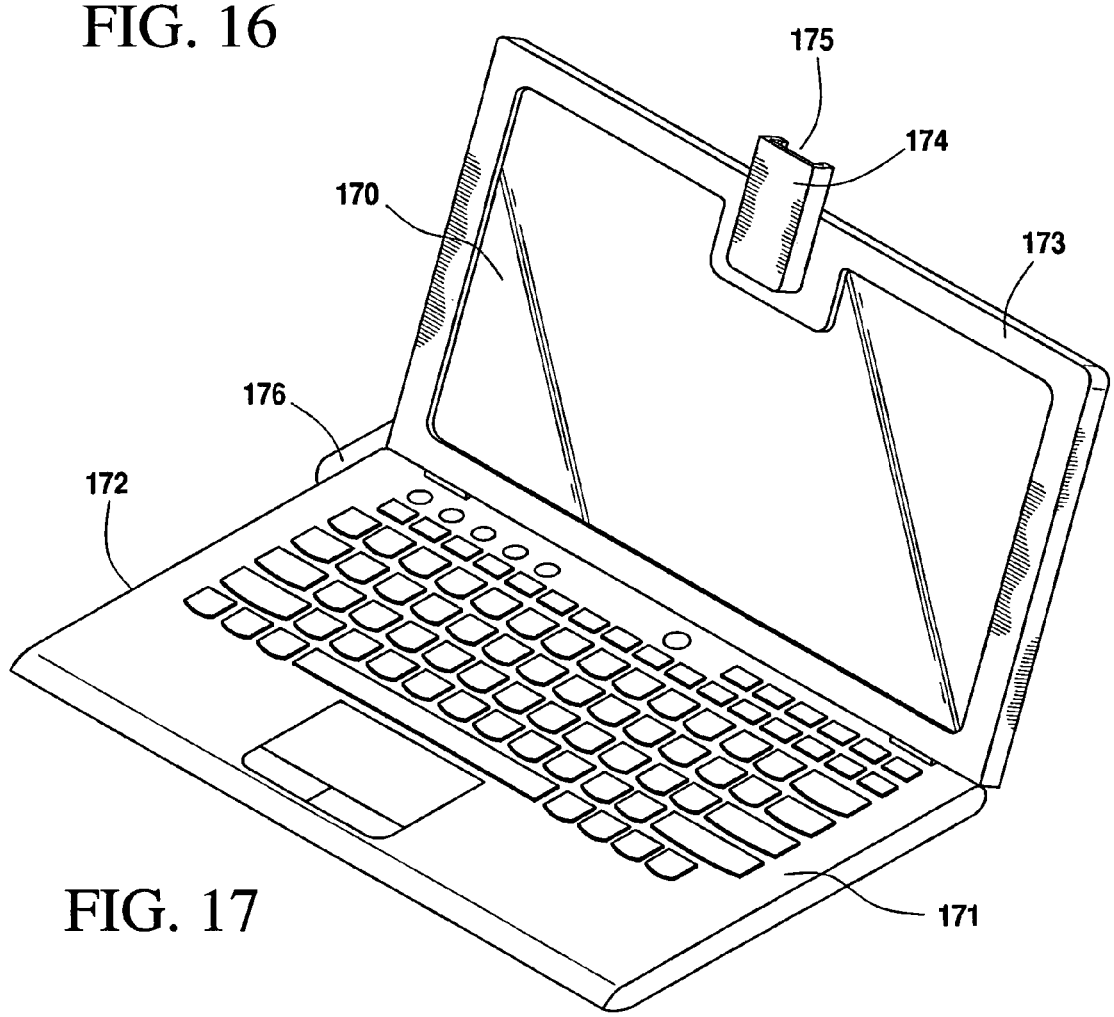
FIG. 17 is a simplified partial perspective view of the front of a laptop computer with a coupler assembled thereto, according to yet another alternative embodiment of the invention.

FIG. 17 is a simplified perspective view of the front of a laptop computer 171 with a coupler 173 installed thereon, according to yet another alternative mobile electronic device embodiment of the invention. In this embodiment, the image sensor lens is located centrally above the display screen 170 of the laptop computer 171, for example, and the electrical connector of the computer is located at a side 172 adjacent the rear of the computer body. The adjunct or frame 173 is fitted over the display screen to place its receptacle 174 for the cartridge (not shown) of the assay apparatus such that the sample contained in a transparent reservoir of the cartridge to be assayed will be positioned directly over the image sensor lens when the cartridge is inserted fully into the opening 175 of the receptacle. Here, the coupler 173 is shaped to reveal the display screen 170 of computer 171, so as to allow substantially unobstructed viewing of assay results and control of functions of the computer on its touch-sensitive screen or allied keyboard. An electrical connector on a pivotable leg 176 of the coupler is arranged to enable mating with the electrical connector of the computer. Here again, the arrangement of components and the operation of the compact portable optical assay apparatus of FIG. 17 corresponds to that described above for the smartphone embodiments, the only difference being that in this example the mobile electronic device is a laptop computer.

A presently contemplated best mode of practicing the invention has been disclosed herein, but variations and modifications will become apparent to those skilled in the art from consideration of the foregoing disclosure, without departing from the spirit and scope of the invention. Accordingly, it is intended that the invention be defined by the following claims and the principles of applicable law.

What is claimed is:

1. A compact portable optical assay system, comprising a mobile electronic device having a battery coupled to an electrical connector accessible from outside the device, and having an optical signal sensor; and an optical assay portion including a light source, a mechanical coupler to couple and decouple the assay portion to and from the device, and a receptacle for a succession of samples from among biological, clinical, environmental, and foodstuff materials to be assayed; each sample labeled with one or more fluorophores to emit optical signals from analytes bound thereto and sought to be detected, if present in the sample, when illuminated by the light source, the coupler being configured to encompass substantially the entire device when fully coupled thereto and thereby to position a sample, when present in said receptacle, in an optical path with both said light source and said optical signal sensor of the device said coupler having an electrical connector arranged and adapted to mate with the electrical connector of the device as the assay portion and the device are fully coupled with the coupler, to assist in securing the two together for stability of both the coupling thereof and the position of the sample in said optical path, and to power both the device and the light source of the assay portion from the device battery, the optical signal sensor being adapted for selective energization by the battery and thereupon to activate the light source to illuminate the sample, whereby to detect analytes in the sample under assay from optical signals captured by the sensor.

2. The system of claim 1, wherein the sensor is responsive to wavelength of optical signals to identify each analyte among cellular, chemical, biochemical, biological, and particulate analytes present in an assayed sample.

3. The system of claim 1, wherein the optical path lies in a first orientation between the light source and the sample, and in a second orientation between the sample and the sensor, with the sample present in the receptacle.

4. The system of claim 1, wherein the receptacle is adapted to receive a succession of transparent cartridges having one or more aligned reservoirs for containment of each respective sample to be assayed singly in said optical path.

5. The system of claim 1, wherein the device includes a display to enable viewing of results of analysis of the captured optical signals, data processing to provide the analysis, memory to enable storage of data resulting from the analysis for subsequent viewing, and wireless transmission capability to enable transmission of said data, analysis and results from the device to a remote location.

6. The system of claim 1, wherein the device includes software for processing data representative of said captured optical signals.

7. The system of claim 4, wherein said light source for said illumination of the sample to be assayed is mounted on one of said receptacle and a cartridge for a sample under assay.

8. The system of claim 1, wherein the device is a smartphone.

9. The system of claim 1, wherein the device is a tablet computer.

10. The system of claim 1, wherein the device is a laptop computer.

11. Compact apparatus for facilitating the performance of optical assays, comprising a mobile electronic device battery-powered for wireless communication with remote locations, said device having an electrical connector to its battery and having an image sensor; and an assay portion having a mechanical coupler including a receptacle for loading samples containing analytes to be assayed, a light source for illuminating a loaded sample with light conducive to the assay, and a container for substantially fully enclosing said device; said coupler having an electrical connector arranged and adapted to mate with the electrical connector of the device when the device is substantially fully enclosed by the container to power both the device and the assay portion from the device battery, and further, by virtue of said substantially full enclosure of the device, the receptacle of said coupler being positioned to place a sample loaded therein in a first optical path for illumination by the light source and in a second optical path for image sensor capture of light emitted from the sample in response to said illumination, wherein said emitted light is fluorescence from fluorophore labels bound to analytes in the loaded sample for identification of each analyte from wavelength of the captured fluorescence.

12. The apparatus of claim 11, wherein said light source is selected to illuminate a loaded sample with light of a wavelength selected to excite a fluorophore attached to at least one analyte to fluoresce in a preselected wavelength band for capture thereof by the image sensor.

13. The apparatus of claim 12, wherein said illumination light from the light source is selectable from any of plural wavelength bands.

14. The apparatus of claim 11, wherein said receptacle is adapted to receive and removably retain a reusable transparent cartridge for loading samples confined therein in successive assays.

15. The apparatus of claim 11, wherein said device has a display for viewing assay results.

16. The apparatus of claim 11, wherein said device is a smartphone for wireless transmission of assay results to a remote location.

17. The apparatus of claim 11, wherein said device is adapted to identify analytes from among cellular, chemical, biochemical, biological, and particulate matter present in an assayed sample, from the wavelengths of the captured fluorescence.

18. In combination, a battery-operated wireless mobile smartphone device housing a battery and related electrical connector, an externally-accessible electrical connector to the battery, a camera including an image sensor with flash function, and digital display, storage, analysis and transmission functions of the device; and an optical assay apparatus comprising a light source, and a mechanical coupler including an electrical connector adapted to mate with the electrical connector of the device to selectively power the light source from the device battery, and a receptacle adapted to sequentially accept multiple samples of materials to be assayed potentially containing target analytes among one or more chemical, biochemical, biological, cellular, and particulate species, wherein target analytes potentially present in a sample are fluorophore-labeled to be identified from optical signals in fluorescence emitted thereby when excited by light of selected wavelength for the target analyte sought to be detected; said coupler constituting a housing adapted to encompass the device therein to retain said assay apparatus and said device in sufficiently closely coupled relationship to urge engagement and mating of the electrical connectors of the coupler and the device, to stabilize the coupled relationship of the assay apparatus and the device, and to enable the light source to be powered by the device battery; said closely coupled relationship serving further to position the receptacle relative to the optics of both the device camera and the light source so that at any time a sample is present in the receptacle, it is positioned for illumination in one direction from the light source and for emission of fluorescence from fluorophore-labeled analytes in the sample in a direction normal to said one direction onto the camera image sensor, whereby when the device camera function is selectively activated from said device battery, the light source is energized to illuminate such sample and thereby excite fluorophore-labeled target analytes potentially present therein according to the wavelength of the illumination, and the activated camera shutter is opened simultaneously to capture fluorescence emitted by said excited target analytes by the exposed camera image sensor as being representative of the content of target analytes in the sample.

19. The combination of claim 18, including at least one transparent cartridge having at least one reservoir to retain a sample therein, said at least one cartridge adapted to be inserted into the receptacle.

20. The combination of claim 18, wherein said flash function is deactivated upon activation of the device camera function.

21. The combination of claim 18, including an optical waveguide for transmitting light emitted from the light source by substantially total internal reflection for maximum incidence of the transmitted light on the sample.

22. The combination of claim 18, wherein the light source is arranged and adapted together with an optical waveguide having dichroic properties in a light path of the receptacle with which both said light source and said device camera are optically related, to direct excitation illumination from the light source in said one direction onto the sample and fluorescence emitted by excited fluorophore-labeled target analytes in said direction normal to said one direction onto the image sensor.

* * * * *